US011723891B2

(12) United States Patent
Snippert et al.

(10) Patent No.: US 11,723,891 B2
(45) Date of Patent: Aug. 15, 2023

(54) DRUG COMBINATIONS FOR USE IN THE TREATMENT OF RAS-MUTANT CANCER

(71) Applicant: UMC Utrecht Holding B.V., Utrecht (NL)

(72) Inventors: Hugo Johannes Gerhardus Snippert, Utrecht (NL); Alexander Eduard Edgar Mertens, Hilversum (NL); Carla Sofia Leiria Verissimo, Utrecht (NL); Johannes Lukas Bos, Bunnik (NL)

(73) Assignee: UMC Utrecht Holding B.V., Utrecht (NL)

( * ) Notice: Subject to any disclaimer, the term of this patent is extended or adjusted under 35 U.S.C. 154(b) by 332 days.

(21) Appl. No.: 17/046,810

(22) PCT Filed: Apr. 12, 2019

(86) PCT No.: PCT/EP2019/059409
§ 371 (c)(1),
(2) Date: Oct. 12, 2020

(87) PCT Pub. No.: WO2019/197605
PCT Pub. Date: Oct. 17, 2019

(65) Prior Publication Data
US 2021/0379007 A1 Dec. 9, 2021

(30) Foreign Application Priority Data
Apr. 12, 2018 (EP) ..................................... 18167004
Oct. 24, 2018 (EP) ..................................... 18202272

(51) Int. Cl.
| | | |
|---|---|---|
| *A61K 31/337* | (2006.01) | |
| *A61P 35/00* | (2006.01) | |
| *A61K 31/166* | (2006.01) | |
| *A61K 31/197* | (2006.01) | |
| *A61K 31/4184* | (2006.01) | |
| *A61K 31/475* | (2006.01) | |
| *A61K 31/496* | (2006.01) | |
| *A61K 31/5377* | (2006.01) | |
| *A61K 45/06* | (2006.01) | |

(52) U.S. Cl.
CPC .......... *A61K 31/337* (2013.01); *A61K 31/166* (2013.01); *A61K 31/197* (2013.01); *A61K 31/4184* (2013.01); *A61K 31/475* (2013.01); *A61K 31/496* (2013.01); *A61K 31/5377* (2013.01); *A61K 45/06* (2013.01); *A61P 35/00* (2018.01)

(58) Field of Classification Search
None
See application file for complete search history.

(56) References Cited

FOREIGN PATENT DOCUMENTS

| WO | WO2014/142660 | 9/2014 |
|---|---|---|
| WO | WO2016/144635 | 9/2016 |

OTHER PUBLICATIONS

Verissimo, C.S., Overmeer, R.M., Ponsioen, B., Drost, J., Mertens, S., Verlaan-Klink, I., Gerwen, B.V., van der Ven, M., Wetering, M.V., Egan, D.A., et al. (2016). Targeting mutant RAS in patient-derived colorectal cancer organoids by combinatorial drug screening. Elife 5. e18489.
Sun, C., Hobor, S., Bertotti, A., Zecchin, D., Huang, S., Galimi, F., Cottino, F., Prahallad, A., Grernrum, W., Tzani, A., et al. (2014). Intrinsic resistance to MEK inhibition in KRAS mutant lung and colon cancer through transcriptional induction of ERBB3. Cell Rep 7, 86-93.
Walters Dustin M et al: "Inhibition of the Growth of Patient-Derived Pancreatic Cancer Xenografts with the MEK Inhibitor Trametinib Is Augmented by Combined Treatment with the Epidermal Growth Factor Receptor/HER2 Inhibitor Lapatinib", Neopl, Neoplasia Press, Ann Arbor, MI, US, vol. 15, No. 2, Feb. 1, 2013 , pp. 143-155, ISSN: 1522-8002, DOI: 10.1593/NEO.121712.
Jänne, Pasi A, et al : "Selumetinib plus docetaxel for KRAS-mutant advanced non-small-cell lung cancer: a randomised, multicentre, placebocontrolled, phase 2 study". The Lancet Oncology, vol. 14, No. 1, Jan. 1, 2013, pp. 38-47, Amsterdam, NL ISSN: 1470-2045, DOI: 10.1016/SI470-2045(12)70489-8.
S. Okumura et al: "Molecular Pathways: The Basis for Rational Combination Using MEK Inhibitors in KRAS-Mutant Cancers", Clinical Cancer Research, vol. 20, No. 16, Aug. 15, 2014 pp. 4193-4199, US ISSN: 1078-0432, DOI:10.1158/1078-0432.CCR-13-2365.
Christopher M. Mahaffey et al: "Schedule-Dependent Apoptosis in K-ras Mutant Non-Small-Cell Lung Cancer Cell Lines—Treated with Docetaxel and Erlotinib: Rationale for Pharmacodynamic Separation", Clinical Lung Cancer, vol. 8, No. 9, Nov. 1, 2007 pp. 548-553, US ISSN: 1525-7304, DOI: 10.3816/CLC. 2007.n.041.
Luigi Formisano et al: "Src inhibitors act through different mechanisms in Non-Small Cell Lung Cancer models depending on EGFR and RAS mutational status", Oncotarget, vol. 6, No. 28, Sep. 22, 2015, DOI: 10.18632/oncotarget.4636.

(Continued)

*Primary Examiner* — Brian J Davis
(74) *Attorney, Agent, or Firm* — N.V. Nederlandsch Octrooibureau

(57) ABSTRACT

The invention relates to the combined use and to a combination of either a microtubule targeting agent or a Src kinase inhibitor, a Raf-MEK-ERK pathway inhibitor and an EGFR and/or ERBB2 inhibitor for use in the treatment of RAS-mutant cancer. The invention further relates to a method of treating RAS-mutant cancers and to a method of testing a combination comprising of a either microtubule targeting agent or a Src inhibitor, a Raf-MEK-ERK pathway inhibitor and an EGFR and/or ERBB2 inhibitor on a tumor organoid. In particular, the invention relates to the combined use of either a microtubule targeting agent or a Src kinase inhibitor with: an inhibitor of the Raf-MEK-ERK pathway and at least one of an inhibitor of both EGFR and ERBB2 and a combination of an EGFR inhibitor and an ERBB2 inhibitor in the treatment of RAS mutant cancer.

13 Claims, 4 Drawing Sheets

(56) References Cited

OTHER PUBLICATIONS

Blagoev, K.B., Wlkerson, J., Burotto, M., Kim, C., Espinal-Dominguez, E., Garcia-Alfonso, P Alimchandani, M., Miettinen, M., Blanco-Codesido, M., and Fojo, T. (2017). Neutral evolution of drug resistant colorectal cancer cell populations is independent of their KRAS status. PLoS One 12, e0175484.

Bos, J.L. (1989). ras oncogenes in human cancer: a review. Cancer Res 49, 4682-4689.

Cox, A.D., Fesik, S.W., Kimmelman, A.C., Luo, J., and Der, C.J. (2014). Drugging the undruggable RAS: Mission possible? Nat Rev Drug Discov 13, 828-851.

Eberhard, D.A., Johnson, B.E., Amler, L.C., Goddard, A.D., Heidens, S.L., Herbst, R.S., Ince, W.L., Janne, P.A., Januario, T., Johnson, D.H., et al. (2005). Mutations in the epidermal growth factor receptor and in KRAS are predictive and prognostic indicators in patients with non-small-cell lung cancer treated with chemotherapy alone and in combination with erlotinib. J Clin Oncol 23, 5900-5909.

Hsu, H.C., Thiam, T.K., Lu, Y.J., Yeh, C.Y., Tsai, W.S., You, J.F., Hung, H.Y., Tsai, C.N., Hsu, A., Chen, H.C., et al. (2016). Mutations of KRAS/NRAS/BRAF predict cetuximab resistance in metastatic colorectal cancer patients. Oncotarget 7, 22257-22270.

Jost, M., Chen, Y., Gilbert, L.A., Horlbeck, M.A., Krenning, L., Menchon, G., Rai, A., Cho, M.Y., Stern, J.J., Prota, A.E., et al. (2017). Combined CRISPRi/a-Based Chemical Genetic Screens Reveal that Rigosertib Is a Microtubule-Destabilizing Agent. Mol Cell 68, 210-223 e216.

Karapetis, C.S., Khambata-Ford, S., Jonker, D.J., O'Callaghan, C.J., Tu, D., Tebbutt, N.C., Simes, R.J., Chalchal, H., Shapiro, J.D., Robitaille, S., et al. (2008). K-ras mutations and benefit from cetuximab in advanced colorectal cancer. N Engl J Med 359, 1757-1765.

Prior, I.A., Lewis, P.D., and Mattos, C. (2012). A comprehensive survey of Ras mutations in cancer. Cancer Res 72, 2457-2467.

Van Brummelen, E. (2017). Early clinical development oftargetted anticancer agents. Thesis Utrecht University.

Fig. 2A

| | MTA alone | 20nM/40nM | 60nM/1.2µM | 1µM/7.2nM | 3µM/21.6nM | 20nM/40nM | 100nM/250nM | |
|---|---|---|---|---|---|---|---|---|
| | | Afa/Sel | | Lapa/Tram | | Daco/PD | | |
| | | 89 | 64 | 71 | 32 | 79 | 41 | Anchors alone |
| Vinorelbine 20µM | 41 | 1 | 2 | 0 | 0 | 2 | 2 | |
| Vinorelbine 5µM | 58 | 5 | 4 | 4 | 3 | 4 | 2 | |
| Vinorelbine 1.26µM | 84 | 11 | 3 | 3 | 0 | 8 | 1 | |
| Vinorelbine 316nM | 92 | 49 | 15 | 5 | 1 | 26 | 3 | |
| Vinorelbine 80nM | 78 | 62 | 29 | 21 | 4 | 56 | 12 | |
| Vinorelbine 20nM | 91 | 76 | 60 | 47 | 10 | 69 | 35 | |
| Vinorelbine 5nM | 95 | 77 | 65 | 55 | 23 | 75 | 47 | MTA+anchors |
| Docetaxel 20µM | 90 | 26 | 12 | 8 | 7 | 26 | 7 | |
| Docetaxel 5µM | 91 | 34 | 11 | 12 | 2 | 27 | 9 | |
| Docetaxel 1.26µM | 79 | 39 | 12 | 12 | 6 | 25 | 8 | |
| Docetaxel 316nM | 92 | 41 | 11 | 14 | 5 | 29 | 5 | |
| Docetaxel 80nM | 78 | 44 | 16 | 21 | 5 | 37 | 8 | |
| Docetaxel 20nM | 87 | 56 | 24 | 22 | 7 | 41 | 12 | |
| Docetaxel 5nM | 86 | 69 | 31 | 41 | 20 | 77 | 25 | |

Fig. 2B

| | MTA alone | 20nM/40nM | 60nM/1.2µM | 1µM/7.2nM | 3µM/21.6nM | 20nM/40nM | 100nM/250nM | |
|---|---|---|---|---|---|---|---|---|
| | | Afa/Sel | | Lapa/Tram | | Daco/PD | | |
| | | 100 | 100 | 100 | 100 | 100 | 90 | Anchors alone |
| Rigosertib 20µM | 95 | 5 | 0 | 0 | 0 | 0 | 0 | |
| Rigosertib 5µM | 100 | 5 | 0 | 0 | 0 | 0 | 0 | |
| Rigosertib 1.26µM | 100 | 5 | 0 | 0 | 0 | 0 | 0 | |
| Rigosertib 316nM | 100 | 20 | 0 | 20 | 0 | 20 | 0 | |
| Rigosertib 80nM | 100 | 60 | 40 | 60 | 5 | 60 | 0 | |
| Rigosertib 20nM | 100 | 100 | 100 | 100 | 95 | 95 | 95 | |
| Rigosertib 5nM | 100 | 100 | 100 | 100 | 100 | 95 | 100 | MTA+anchors |
| Paclitaxel 20µM | 100 | 0 | 0 | 5 | 0 | 0 | 0 | |
| Paclitaxel 5µM | 100 | 5 | 5 | 10 | 5 | 20 | 0 | |
| Paclitaxel 1.26µM | 100 | 40 | 15 | 50 | 10 | 50 | 15 | |
| Paclitaxel 316nM | 90 | 60 | 20 | 95 | 50 | 85 | 30 | |
| Paclitaxel 80nM | 60 | 60 | 50 | 100 | 80 | 95 | 80 | |
| Paclitaxel 20nM | 100 | 90 | 60 | 100 | 100 | 100 | 95 | |
| Paclitaxel 5nM | 100 | 100 | 100 | 100 | 100 | 100 | 100 | |

Fig. 2C

|  |  | Dasatinib alone | 20nM/400nM | 65nM/1.2μM | 1μM/7.2nM | 3μM/21.6nM | 25nM/40nM | 100nM/200nM |  |
|---|---|---|---|---|---|---|---|---|---|
|  |  |  | Afa/Sel | | Lapa/Tram | | Daco/PD | | |
|  |  | 100 | 100 | 100 | 100 | 100 | 100 | 90 | Anchors alone |
| | 20μM | 0 | 0 | 0 | 0 | 0 | 0 | 0 | |
| | 5μM | 60 | 10 | 0 | 5 | 0 | 5 | 0 | |
| Dasatinib (Src) | 1.26μM | 95 | 30 | 0 | 15 | 0 | 10 | 0 | Dasatinib + anchors |
| | 316nM | 100 | 40 | 5 | 50 | 0 | 20 | 1 | |
| | 80nM | 100 | 90 | 20 | 80 | 5 | 80 | 5 | |
| | 20nM | 100 | 100 | 95 | 100 | 70 | 100 | 50 | |
| | 5nM | 100 | 100 | 100 | 100 | 95 | 100 | 80 | |

Cmax ≈ 120nM

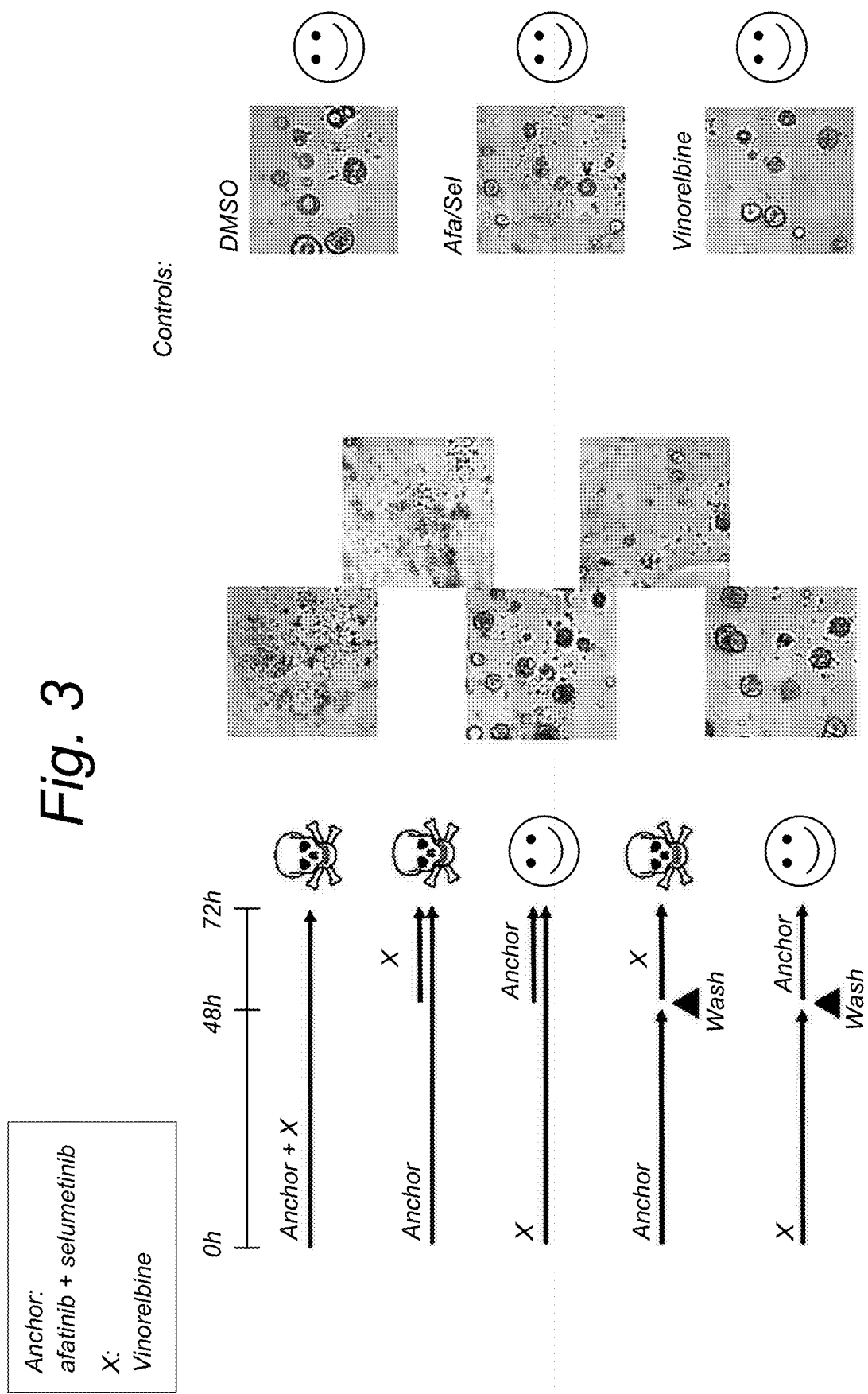

DRUG COMBINATIONS FOR USE IN THE TREATMENT OF RAS-MUTANT CANCER

FIELD OF THE INVENTION

The present invention relates to the field of medicine and molecular diagnostics. In particular, it relates to novel pharmaceutical combinations comprising an inhibitor of the Raf-MEK-ERK pathway, and at least one of an inhibitor of both EGFR and ERBB2 and a combination of an EGFR inhibitor and an ERBB2 inhibitor and a microtubule targeting agent or a Src kinase inhibitor for use in the treatment of RAS-mutants cancers.

BACKGROUND OF THE INVENTION

Cancer is one of the leading causes of death in the Europe and the United States. Despite recent advances in understanding mechanisms involved in cancer and in diagnosis and treatment, drug therapies for metastatic disease are often palliative in nature. Drug therapies seldom offer a long-term cure. There is a constant need for new methods of treatment, either in the form of monotherapy or in the form of combination treatment, combining different new or known drugs as first line therapy, and as second line therapies in treatment of resistant tumors.

Multiple mutational mechanisms may lead to the development of cancer and mutational mechanisms associated with some cancers may differ between one tissue type and another. However, in a number of genes mutations are rather frequently observed. These commonly mutated "cancer driver genes" include for instance the three members (KRAS, NRAS and HRAS) of the RAS family, particularly KRAS and NRAS, p53, BRAF, BCR-ABL, ALK, EGFR. These and other mutated genes have been under extensive analysis for drugs that specifically inhibits the mutated protein. This has been rather successful for mutant BRAF in melanoma, and BCR-ABL for chronic myeloid leukemia.

Mutations in RAS genes occur in 15-20% of all cancers (Bos, 1989), but most notably in pancreatic cancer (90%), colorectal cancer (50%), adenocarcinoma of the lung (30%). For these tumors the far majority of the mutations occur in KRAS codons 12, 13 and 61. In acute myeloid leukemia and melanoma the predominant mutant RAS protein is NRAS. Mutation of HRAS occurs relatively infrequent. The clinical relevance of these mutations lies in the observation that agents that target the EGFR receptor, like cetuximab for colon cancer and erlotinib for lung cancer, are ineffective in mutant RAS colon cancer or lung cancer (Eberhard et al., 2005; Karapetis et al., 2008). Therefore, the mutation status of RAS has to be determined prior to administration and patients with mutant KRAS cancer are excluded from therapy. When these drugs are used for normal RAS cancers, resistance is frequently observed due to the appearance of mutant RAS tumor cells, although Ras independent mechanisms of resistance occur as well (Blagoev et al., 2017; Hsu et al., 2016). Importantly, cancers that do not responds to inhibitions of the EGFR receptor are phenotypically similar to mutant RAS, as no other targeted treatment is available. So there is an urgent clinical need for the development of drugs that inhibit mutant RAS cancers, Although extensively tried, direct inhibition of mutant Ras proteins has been unsuccessful thus far (Cox et al., 2014).

As an alternative approach, inhibitors that block mutant RAS-induced signaling pathways, including inhibitors of RAF, MEK and ERK have been tested, but currently these inhibitors act poorly on mutant RAS containing tumors.

Previously, it has been reported that the combination of an inhibitor to both EGFR and ERBB2, like afatinib, in combination with an inhibitor to MEK1 and 2, like selumetinib, synergizes in the killing of KRAS-mutant colon tumor cell lines and KRAS-mutant lung tumor cell lines (Sun et al., 2014). We subsequently found using tumor organoids from colorectal cancer patients that in KRAS-mutant colorectal cancer organoids this combination does inhibit cell proliferation, but cells remain viable and rapidly start to proliferate once the drug was washed away. Thus, the effect is largely cytostatic, rather than cytotoxic, predicting limited effects in patients (Verissimo et al., 2016). Furthermore, these studies showed that an inhibitor of ERK was as effective as an inhibitor of MEK in the combination, showing that inhibition of ERK is the crucial event. This indicates that all inhibitors that interfere in RAS-induced ERK activity, e.g. inhibitors of either RAS, Raf1, B-raf, ERK can replace the MEK inhibitor in the combination (Verissimo et al., 2016, supra). Similarly, it is predicted that any inhibitor that inhibits signaling downstream from the EGFR and ERBB2 receptors will be effective in the combination with an inhibitor of the Raf-MEK-ERK pathway.

Although, phase 1 clinical studies in mutant KRAS colorectal cancer established a recommended phase 2 dose (RP2D) of the combined treatment of the drugs afatinib (EGFR/ERBB2 inhibitor) and selumetinib (MEK inhibitor), lapatinib (EGFR/ERBB2 inhibitor) and trametinib (MEK inhibitor) and dacomitinib (EGFR/ERBB2 inhibitor) and PD-0325901 (MEK inhibitor), follow-up studies were terminated due to lack of response (Van Brummelen, 2017).

In one attempt a third drug was added to the combination EGFR/ERBB2 and MEK. This drug, the BCL-XL inhibitor navitoclax gave a strong synergistic effect on mutant KRAS colon tumor organoids, but these studies were halted, as preliminary studies indicated toxicity in mice (Verissimo et al., 2016, supra).

WO2014/142660 A1 describes a combination of a MEK-inhibitor, an EGFR-inhibitor and an ERBB2-inhibitor (WO2014/142660 A1); this combination while exhibiting synergistic behavior in the inhibition of cell proliferation of KRAS mutant colon cells, is rather ineffective in inducing apoptosis (Verissimo et al., 2016, supra).

It is a goal of the current invention to provide for new and improved methods of treatment of RAS-mutant cancers, including, KRAS-mutant cancers, as well as to provide for products and therapeutically pharmaceutical combinations for use in these RAS-mutant cancers.

SUMMARY OF THE INVENTION

In a first aspect, the invention relates to a combination comprising an inhibitor of the Raf-MEK-ERK pathway and at least one of an inhibitor of both EGFR and ERBB2 and a combination of an EGFR inhibitor and an ERBB2 inhibitor for use in the treatment of RAS-mutant cancer wherein the combination is administered simultaneously, separately or sequentially with a microtubule targeting agent or a Src inhibitor.

In a second aspect the invention relates to a combination comprising of an inhibitor of the Raf-MEK-ERK pathway and at least one of an inhibitor of both EGFR and ERBB2 and a combination of an EGFR inhibitor and an ERBB2 inhibitor, wherein the combination further comprises a microtubule targeting drug or a Src inhibitor.

In a third aspect, the invention relates to a method for treating a RAS-mutant cancer in a subject comprising administrating to the subject an effective amount of a combination comprising an inhibitor of the Raf-MEK-ERK pathway and at least one of an inhibitor of both EGFR and ERBB2 and a combination of an EGFR inhibitor and an ERBB2 inhibitor, wherein the combination is administered simultaneously, separately or sequentially with a microtubule targeting agent or a Src inhibitor.

In a fourth aspect the invention relates to a method for testing a combination of: an inhibitor of the Ras-MEK-ERK pathway, at least one of an inhibitor of both EGFR and ERBB2 and a combination of an EGFR inhibitor and an ERBB2 inhibitor and a microtubule targeting agent or a Src inhibitor to be used in the treatment of a patient suffering from a RAS-mutant cancer, wherein the method comprises the step of the combined, separate or sequential addition of the combination to a tumor organoid derived from the patient and determining the effect of the combination on the growth of the tumor organoid.

DESCRIPTION OF THE INVENTION

Definitions

Unless defined otherwise, technical and scientific terms used herein have the same meaning as commonly understood by one of ordinary skill in the art to which this disclosure belongs. One skilled in the art will recognize many methods and materials similar or equivalent to those described herein, which could be used in the practice of the present invention. Indeed, the present invention is in no way limited to the methods and materials described.

For purposes of the present invention, the following terms are defined below.

As used herein, the singular forms "a," "an" and "the" include plural referents unless the context clearly dictates otherwise. For example, a method for administrating a drug or an agent includes the administrating of a plurality of molecules (e.g. 10's, 100's, 1000's, 10's of thousands, 100's of thousands, millions, or more molecules).

As used herein, the term "and/or" indicates that one or more of the stated cases may occur, alone or in combination with at least one of the stated cases, up to with all of the stated cases.

As used herein, with "At least" a particular value means that particular value or more. For example, "at least 2" is understood to be the same as "2 or more" i.e., 2, 3, 4, 5, 6, 7, 8, 9, 10, 11, 12, 13, 14, 15, . . . , etc.

As used herein "cancer" and "cancerous", refer to or describe the physiological condition in mammals that is typically characterized by unregulated cell growth. Examples of cancer include, but are not limited to, colon cancer and lung cancer. Cancer is also referred to as malignant neoplasm.

As used herein, "in combination with" is intended to refer to all forms of administration that provide a first drug together with a further (second, third) drug. The drugs may be administered simultaneous, separate or sequential and in any order. Drugs administered in combination have biological activity in the subject to which the drugs are delivered.

As used herein "simultaneous" administration refers to administration of more than one drug at the same time, but not necessarily via the same route of administration or in the form of one combined formulation. For example, one drug may be provided orally whereas the other drug may be provided intravenously during a patient's visit to a hospital. Separate includes the administration of the drugs in separate form and/or at separate moments in time, but again, not necessarily via the same route of administration. Sequentially indicates that the administration of a first drug is followed, immediately or in time, by the administration of the second drug.

As used herein, "colon cancer", or "colorectal cancer" relates to a cancer from uncontrolled cell growth in the colon or rectum, or in the appendix.

As used herein, "to comprise" and its conjugations is used in its non-limiting sense to mean that items following the word are included, but items not specifically mentioned are not excluded. It also encompasses the more limiting "to consist of".

A used herein "compositions", "products" or "combinations" useful in the methods of the present disclosure include those suitable for various routes of administration, including, but not limited to, intravenous, subcutaneous, intradermal, subdermal, intranodal, intratumoral, intramuscular, intraperitoneal, oral, nasal, topical (including buccal and sublingual), rectal, vaginal, aerosol and/or parenteral or mucosal application. The compositions, formulations, and products according to the disclosure invention normally comprise the drugs (alone or in combination) and one or more suitable pharmaceutically acceptable excipients.

As used herein, "an effective amount" is meant the amount of an agent required to ameliorate the symptoms of a disease relative to an untreated patient. The effective amount of active agent(s) used to practice the present invention for therapeutic treatment of a cancer varies depending upon the manner of administration, the age, body weight, and general health of the subject. Ultimately, the attending physician or veterinarian will decide the appropriate amount and dosage regimen. Such amount is referred to as an "effective" amount. Thus, in connection with the administration of a drug which, in the context of the current disclosure, is "effective against" a disease or condition indicates that administration in a clinically appropriate manner results in a beneficial effect for at least a statistically significant fraction of patients, such as an improvement of symptoms, a cure, a reduction in at least one disease sign or symptom, extension of life, improvement in quality of life, or other effect generally recognized as positive by medical doctors familiar with treating the particular type of disease or condition.

As used herein, "lung cancer" is cancer that accounts for almost one third of cancer deaths, and is broadly classified into two types: non-small-cell lung cancer and small cell lung cancer. Non-small-cell lung cancer (NSCLC) comprises 80-85% of lung cancer cases and different types of NSCLC are named based on the kinds of cells found in the cancer and how the cells look under a microscope. NSCLC comprises squamous cell carcinoma, large cell carcinoma, which begins in several types of large lung cells and adenocarcinoma, which begins in the cells that line the alveoli of the lung and make substances such as mucus.

As used herein, "pancreatic cancer" relates to a cancer from uncontrolled cell growth in the pancreas.

As used herein, "mutant RAS cancer" relates to all cancers with a mutation in either KRAS, NRAS or HRAS, as well as tumors resistant to drugs that are ineffective to mutations in either KRAS, NRAS or HRAS, such as resistance to cetuximab for colon cancer and resistance to erlotinib for adenocarcinoma of the lung.

As used herein, "an inhibitor of the Raf-MEK-ERK pathway", relates to any inhibitor that inhibits a component of this pathway, which is directly downstream from mutant Ras, being either Raf1, B-raf, MEK1 and 2 or ERK1 and 2, separately or simultaneously. In the examples herein show proof-of-concept for inhibitors of the Raf-MEK-ERK pathway using inhibitors of either MEK1 and MEK2. The other inhibitors of this pathway therefore have similar effects.

As used herein, "microtubule targeting agents" relates to any drug that interferes in microtubule dynamics, for instance, by stabilization of microtubules or by destabilization of microtubules.

As used herein, Src kinases comprise the tyrosine kinases Src, Fyn and Yes.

As used herein, "a Src inhibitor" relates to any drug that interferes in the Src kinase and/or the related FAK signaling pathway. It may inhibit a single or multiple members of either the Src or FAK family of kinases, or simultaneously members of the Src kinase and FAK kinase families.

DETAILED DESCRIPTION OF THE INVENTION

As demonstrated herein the combination of either a microtubule targeting agents or a Src inhibitor, with a MEK-inhibitor and at least one of an inhibitor of both EGFR and ERBB2 and a combination of an EGFR inhibitor and an ERBB2 inhibitor manifests an unexpected and strong synergistic, therapeutic effect on the treatment of RAS-mutant cancers as determined on patient-derived tumor organoids. Importantly, the effect in organoids was also observed when the combination of the MEK-inhibitor and the inhibitor of at least one of EGFR and ERBB2 was given first, followed by a single treatment with a microtubule targeting agent, indicating that sequential addition is effective as well.

In a first aspect there is provided for a combination comprising an inhibitor of the Raf-MEK-ERK pathway and at least one of an inhibitor of both EGFR and ERBB2 and a combination of an EGFR inhibitor and an ERBB2 inhibitor for use in the treatment of RAS-mutant cancer wherein the combination is administered simultaneously, separately or sequentially with a microtubule targeting agent or a Src inhibitor.

The term "combination" as used herein is understood to refer to a combination therapy (as opposed to a monotherapy) wherein treatment comprises the use or administration of the inhibitor of the Raf-MEK-ERK pathway with the use or administration of with at least one of an inhibitor of both EGFR and ERBB2 and a combination of an EGFR inhibitor and an ERBB2 inhibitor.

Thus, in a combination therapy according to the invention the components of the combination can be administered simultaneously, separately or sequentially. The components of the combination can thus be formulated in a single composition, or the components can be formulated in at least two separate formulations. The combination can be a single product, comprising a single composition or comprising the components formulated in at least two separate formulations. Alternatively, the combination can be at least two different products that can from one or more than one supplier.

Ras proteins are proto-oncogenes that are frequently mutated in human cancers. They are encoded by three ubiquitously expressed genes: HRAS, KRAS and NRAS. These three RAS genes are one of the most common oncogenes in human cancer; mutations that permanently activate Ras are found in 15-20% of all human tumors and up to 90% in certain types of cancer (e.g., pancreatic cancer). The term "RAS-mutant cancer" is well-known to the skilled person; RAS-mutant cancer are cancers that comprise a mutation in the genes: KRAS, NRAS, and HRAS, and which mutation preferably permanently activates the encoded Ras protein. A comprehensive overview of RAS mutations in cancer was reported by (Prior et al., 2012).

Although RAS-mutant cancer most frequently comprises a mutated KRAS gene, all three Ras proteins, H-ras, K-ras and N-ras behave similarly. The unmutated Ras proteins act as a molecular on/off switch. Once it is turned on it recruits and activates proteins necessary for the propagation of growth factor and other receptors signals, such as c-Raf and PI 3-kinase. As such, the unmutated Ras proteins perform essential function in normal tissue signaling. In the mutant Ras-protein, the switch activity is constitutively "on" resulting in aberrant signaling. Indeed, the mutation of a RAS gene is an essential step in the development of many cancers.

RAS-mutant cells promote oncogenesis due to being mutationally activated, in most cases, at codon 12, 13 and 61. In total forty-four separate point mutations have been characterized in RAS isoforms, with 99.2% in codons 12, 13 and 61. Therefore, a preferred KRAS-mutant cancer to be treated in accordance with the invention is a KRAS-mutant cancer comprises a KRAS gene encoding a K-ras protein that is mutationally activated by a mutation in at least one of codon 12, 13 and 61. The term "KRAS-mutant cancer", and therefore KRAS-mutant lung cancer or KRAS-mutant colon cancer, is well known to the skilled person. Examples of RAS-mutant cancers are KRAS-mutant colon, KRAS-mutant lung cancer, KRAS-mutant pancreatic cancer, KRAS-mutant mucinous adenoma, KRAS-mutant ductal carcinoma, or NRAS-mutant leukemia, NRAS-mutant melanoma (Prior et al., 2012). In one preferred embodiment of the invention the RAS-mutant cancer is KRAS-mutant colon, KRAS-mutant lung cancer, KRAS-mutant pancreatic cancer, KRAS-mutant mucinous adenoma, KRAS-mutant ductal carcinoma, or NRAS-mutant leukemia, NRAS-mutant melanoma. Microtubule targeting drugs or microtubule targeting agents used in the clinic as anti-cancer drugs either stabilize or destabilize microtubules, affecting microtubule dynamics. Originally these drugs were considered to be functioning by inhibiting mitosis, a process that requires microtubule to separate chromosomes orderly. However, more recent data suggest that microtubule targeting drugs may induce apoptosis independent of mitosis ((Komlodi-Pasztor et al., 2011).

Mitogen-activated protein kinase (MEK) comprises both MEK1 and MEK2: MAP/ERK kinase 1, MEK1, PRKMK1, MAPKK1, MAP2K1, MKK1 are the same enzyme, known as MEK1, MAP/ERK kinase2, MEK2, PRKMK2, MAPKK2, MAP2K2, MKK2 are the same enzyme, known as MEK2. MEK1 and MEK2, together MEK, can phosphorylate serine, threonine and tyrosine residues in protein or peptide substrates. To date, few cellular substrates of MEK isoforms have been identified. Methods to determine MEK-inhibitors (inhibiting MEK 1, MEK2 or both) are known in the art, for example as described in detail in EP2496575.

In one embodiment of the invention the MEK-inhibitor is one or more of sorafenib, PD-0325901 (Pfizer), trametinib, UO126-EtOH, PD184352, PD98059, BIX 02189, pimasertib (AS-703026, BIX 02188, TAK-733, binimetinib (MEK163, ARY-162, ARRY-2438162, PD318088, honokiol, SL-327, refametinib (RDEA119, Bay 86-9766, GDC-0623, APS-2-79-HCI, cobimetinib (GCD-0973, RG7420) (Genentech), BI-847325, AZD-8330 (AstraZeneca), RG-7167 (Roche/Chugai), RG-7304 (Roche), CIP-137401 (Cheminpharma), WX-554 (Wilex; UCB), SF-2626 (Semafore Pharmaceuticals Inc), R0-5068760 (F Hoffmann-La Roche AG), R0-4920506 (Roche), G-573 (Genentech) and G-894 (Genentech), N-acyl sulfonamide prodrug GSK- 2091976A (GlaxoSmithKline), 81-847325 (Boehringer Ingelheim), WYE-130600 (Wyeth/Pfizer), ERK1-624, ERK1-2067, ERK1-23211, AD-GL0001 (ActinoDrug Pharmaceuticals GmbH), selumetinib (AZD6244), MEK-162, derivatives and salts thereof. Preferably, in the compositions, combinations, products and methods according to the invention, the MEK-inhibitor is one or more of selumetinib, trametinib, PD-0325901 and derivatives and/or salts thereof.

The protein kinase Raf comprises both Raf1 (also known as CMD1NN, CRAF, NS5, Raf-1, c-Raf) and B-raf (also known as B-raf1, NS7, RAFB1, BRAF). Raf1 and B-raf can phosphorylate serine and threonine residues in protein or peptide substrates. To date, few cellular substrates of Raf isoforms have been identified, most notably MEK1 and MEK2. Methods to determine Raf inhibitors (inhibiting Raf1, B-raf and mutant B-raf or both) are known in the art.

In one embodiment of the invention the Raf1 inhibitor and/or the B-raf inhibitor is one or more of sorafinib, sorafinib tolysate, vemurafinib, dabrafinib, PLX 4720, CDC-0879, lifirafenib, Raf265, AZ628, SB590885, ZM336372, GW5074, TAK-632, CEP-32496, encorafinib, CCT196969, PLX7904, LY03009120, R05126766, MLN2480, derivatives and salts thereof.

Extracellular signal activated kinase (ERK)) comprises both ERK1 and ERK2: MAPK3, ERT2, HS44KDAP, HUMKER1A, P44ERK1, P44MAPK, PRKM3, p44-ERK1, p44-MAPK are the same enzyme known as ERK1; MAPK1, ERK-2, ERK2, ERT1, MAPK2, P42MAPK, PRKM1, PRKM2, p38, p40, p41, p41mapk, p42-MAPK are the same enzyme known as ERK2. ERK1 and ERK2 can phosphorylate serine and threonine residues in protein or peptide substrates. To date, a number of cellular substrates of MEK isoforms have been identified. Methods to determine ERK-inhibitors (inhibiting ERK 1, ERK2 or both) are known in the art.

In one embodiment of the invention the ERK-inhibitor is one or more of SCH772984, ERK-IN-1, SC1, XMD8-92, LY3214996, ulixertinib (BVD-523), VRT752271, FR180204, DEL-22379, CD-0994, VX-11e and derivatives and salts thereof.

The epidermal growth factor family of receptor tyrosine kinases (ErbBs) plays essential roles in regulating cell proliferation, survival, differentiation and migration. ErbB receptors are expressed in a variety of tissues of epithelial, mesenchymal and neuronal origin, where they play fundamental roles in development, proliferation, differentiation and angiogenesis. These receptors are activated by numerous ErbB-specific ligands that bind the extracellular domains and lead to the formation of both homo- and heterodimers. Activation of these receptors typically occurs via specific ligand binding, resulting in hetero- or homodimerization between receptor family members, with subsequent autophosphorylation of the tyrosine kinase domain. This activation triggers a cascade of intracellular signaling pathways involved in both cellular proliferation and survival. The family comprises four closely related members: Epidermal Growth Factor Receptor (EGFR), ErbB2/Neu/HER2, ErbB3 and ErbB4. Members of this family, including EGFR and HER2, have been directly implicated in cellular transformation. Additionally, EGFR has been demonstrated to play a critical role in cellular growth, differentiation, and survival. Methods to determine ERBB2-inhibitors and EGFR-inhibitors are known in the art, for example as described in detail in EP1877398.

In a treatment of a RAS-mutant cancer in accordance with the invention, an inhibitor of at least one of EGFR and ERBB2 is administered. Preferably, at least one of an inhibitor of both EGFR and ERBB2 and a combination of an EGFR inhibitor and an ERBB2 inhibitor is administered. The term "an inhibitor of at least one of EGFR and ERBB2" is herein understood to include at least a) inhibitors that inhibit either one of EGFR and ERBB2, b) inhibitors that inhibit both EGFR and ERBB2, c) combinations of an inhibitor that inhibits EGFR with an inhibitor that inhibits ERBB2, and any combination of a), b) and c).

Preferably, in a treatment according to the invention, the EGFR-inhibitor is one or more of erlotinib (OSI-744), panitumumab (Abgenix), vandetanib (AstraZeneca), icotinib (hydrochloride; Beta Pharma), CO-1686 (Avila Therapeutics), AZD-4769, poziotinib (Hanmi Pharmaceutical Co Ltd), CUDC-101 (Curis), Exelixis, S-222611 (Shioogi), imgatuzumab (Glycart Biotechnology AG), sapitinib, TAS-2913 (Taiho Pharmaceutical Co Ltd), theliatinib (Hutchison Medipharma Enterprises Ltd), XGFR-2421 (Glycart), HM-617138 (Hanmi Pharmaceutical Co Ltd), epitinib (Hutchison Medipharma Enterprises Ltd), NRC-2694 (Natco), MLBS-42 (ProQinase GmbH), JRP-890 (Prous Institute for Biomedical Research Sa), cetuximab, AL-6802 (Advenchen Laboratories LLC), TAK-285 (Takeda), BGB-102 (Johnson & Johnson), AEE-788 (Novartis), gefitinib, DMS-3008 (Domantis Ltd), TX-2036 (University of Tokushima), KI-6783, KI-6896 (Kirin Brewery Co Ltd), gefitinib (ZD1839), lapatinib, lapatinib ditosylate (GW-572016), afatinib (BIBW2992), neratinib, canertinib (CI-1033), AG-490, CP724714, dacomitinib (PF299804, PF299), WZ-4002, sapitinib (AZD8931), CUDC-101, AG-1478, PD153035 HCl, pelitinib (EKB-569), AC480 (BMS-599626), AEE788, AP26113-analog (ALK-IN-1), OSI-420, WZ3146, Her2 inhibitor-1, AST-1306, rociletinib (CO-1686, AVL-301), genistein, varlitinib, icotinib. WHI-P154, daphnetin, PD168393, CNX-2006, tyrphostin 9, AG-18, osimertinib (AZD9291), olmutinib (HM61713, BI1482694), cetuximab, norcantharidin, EAI045, afatinib dimaleate, CL-387785 (EKI-785), lidocaine hydrochloride, nazartinib (EGF816, NVS-816), NSC228155, AZ5104, lifirafinib (BGB-283), naquotinib (ASP8273), AZD3759, and derivatives and/or salts thereof. Preferably, in the compositions, combinations, products and methods according to the invention, the EGFR-inhibitor is one or more of lapatinib, afatinib, dacometinib and derivatives and/or salts thereof.

Examples of drugs that inhibit EGFR include Tarceva™ (also known as erlotinib; OSI-774). It is a selective inhibitor of EGFR tyrosine kinase. Erlotinib inhibits human EGFR tyrosine kinase with an 1050 of 2 nM (0.786 mg/ml) in an in vitro enzyme assay.

Preferably, in a treatment according to the invention the ERBB2-inhibitor is one or more of: pertuzumab, trastuzumab, neratinib, allitinib tosylate, CUDC-101, BT-2111, margetuximab, exelixis, NT-004 or NT-113, S-222611, AG879, mubritinib, AC-480, sapitinib, MM-111, PR-610, cipatinib, duocarmycin, prolanta, varlitinib, kahalalide F, TrasGEX, masoprocol, erbicinumab, HuMax-Her2, CP-724714, COVA-208, and pazopanib, AEE-788, canertinib, pelitinib, BMS-690514, lapatinib, lapatinib ditosylate (GW-572016), afatinib (BIBW2992), neratinib, canertinib (CI-1033), AG-490, CP724714, sapitinib (AZD 8931), dacomitinib (PF299804, PF299), WZ-4002, sapitinib (AZD8931), CUDC-101, mubritinib (TAK 165), AC480 (BMS-599626), AEE788, HER2 inhibitor 1, TAK-285, tyrphostin AG 879, irbinitinib (ARRAY-380, ONT-380) poziotinib (HM781-36B), derivatives and salts thereof. Preferably, in the compositions, combinations, products and methods according to the invention, the ERBB2-inhibitor is one or more of lapatinib, afatinib, dacometinib and derivatives and/or salts thereof.

In other words, such drug may be a pan-ERBB inhibitor, inhibiting more than one ERBB at the same time, for example inhibiting the tyrosine kinases of both ERBB1 (EGFR), ERBB2 (HER2) and ERBB4. Other examples are dual-ERBB inhibitors, for example inhibiting ERBB1 (EGFR) and ERBB2 (HER2).

Preferably, in a treatment according to the invention, the EGFR-inhibitor and the ERBB2-inhibitor are one and the same compound, i.e. a single drug, compound or molecule that inhibits both EGFR and ERBB2. Examples of inhibitors that inhibit both EGFR and ERBB2 include lapatinib, lapatinib ditosylate (GW-572016), afatinib (BIBW2992), neratinib, canertinib (CI-1033), sapitinib (AZD 8931), dacomitinib (PF299804, PF299), CUDC-101, mubritinib (TAK 165), TAK-285, poziotinib (HM781-36B).

In one embodiment of the invention microtubule targeting drugs can be at least one of vinca alkaloid, a taxane, rigosertib, volasertib, plinabulin, lexibulin, or derivatives thereof compounds.

Vinca alkaloids, a set of anti-mitotic and anti-microtubule alkaloid agents originally derived from the periwinkle plant *Catharanthus roseus* (basionym *Vinca rosea*) and other vinca plants. Examples of vinca alkaloids include vinblastine, vincristine, vindesine, vinorelbine, vincaminol, vineridine, vinflunine, vinburnine, vinpocetine, minovincine, methoxyminovincine, minovincinine, vincadifformine, desoxyvincaminol, vincamajine.

One or more of the above vinca alkaloids may preferably be used in the compositions, combinations, products and methods according to the invention, for example vinblastine, vincristine, vindesine, vinorelbine, vinflunine and derivatives and/or salts thereof.

Taxanes are a class of diterpenes. They were originally identified from plants of the genus Taxus (yews), and feature a taxadiene core. Paclitaxel (Taxol) and docetaxel (Taxotere) are widely used as chemotherapy agents. Examples or taxanes are paclitaxel (Taxol), docetaxel (Taxotere), carbazitaxel (Jevtana) (Sanofi-Aventis), or derivatives or salts thereof. One or more of the above taxanes may preferably be used in the compositions, combinations, products and methods according to the invention, for example paclitaxel and docetaxel and derivatives and/or salts thereof.

Several other microtubule targeting drugs have similarly synergistic effects with the combination of MEK and EGFR/ERBB2 inhibitors, which include rigosertib (Onconova Therapeutics), Volasertib (Boehringer Ingelheim), Plinabulin (BeyondSpring Pharmaceuticals), Lexibulin (YM BioSciences Australia).

Methods to determine microtubule targeting agents are known in the art.

Preferably, in the compositions, combinations, products and methods according to the invention, the microtubule targeting drug is one or more of plinabulin, vinorelbine, vincristine, docetaxel, paclitaxel, rigosertib, vinblastine and derivatives and/or salts thereof. Src inhibitors are a class of inhibitors that target the Src kinase family, a family of non-receptor tyrosine kinases that includes Src, Fyn and Yes. Src family kinases interact with many cellular cytosolic, nuclear and membrane proteins, modifying these proteins by phosphorylation of tyrosine residues. Src kinase inhibitors have been used as anti-cancer drugs in the clinic and can, directly or indirectly, inhibit Src and/or focal adhesion kinase (FAK) kinases.

In one embodiment of the invention the inhibitor of Src kinases can be at least one of dasatinib, saracatinib, bosutinib, KX2-391 (KX-01), NVP-BHG712, PP2, PP121, PP1, MNS (3,4-Methylenedioxy-β-nitrostyrene, MDBN), TPX-0005, WH-4-023, dasatinib monohydrate, CCT196969, MRL-1023, dasatinib hydrochloride, UM-164, SU6656, AD80 (multikinase inhibitor against RAF, BRAF and SRC), CCT196969 (Pan-Raf, anti-SRC) and derivatives and/or salts thereof.

Methods to determine inhibitors of Src kinases are known in the art.

Preferably, in the compositions, combinations, products and methods according to the invention, the inhibitor of Src kinases is at least one of dasatinib, saracatinib, bosutinib and KX2-391 (KX01).

The MEK-inhibitor and the inhibitor of at least one of EGFR and ERBB2 may be administered to the patients either simultaneously, separately or sequentially with the microtubule targeting agent or the Src inhibitor.

For example, in one embodiment of the invention the microtubule targeting agent may be used simultaneously, separately or sequentially with the MEK-inhibitor, and simultaneously, separately or sequentially with the inhibitor of at least one of EGFR and ERBB2. When given separately or sequentially, the order of administration of the drugs can be for example that the Raf-MEK-ERK-Inhibitor is administered first, the EGFR-inhibitor is administered second, and the ERBB-2-inhibitor is administered third and the microtubule targeting agent may be administered last. Any other order of administration of the drugs is also possible. In a preferred embodiment, the Raf-MEK-ERK/EGFR/ERBB2 inhibitors are administered first and the microtubule targeting agent is administered last. In other words, the Raf-MEK-ERK/EGFR/ERBB2 inhibitors are administered before the microtubule targeting agent.

In another embodiment of the invention, the Src inhibitor may be used simultaneously, separately or sequentially with the MEK-inhibitor, and simultaneously, separately or sequentially with the inhibitor of at least one of EGFR and ERBB2. When given separately or sequentially, the order of administration of the drugs can be for example that the Raf-MEK-ERK-Inhibitor is administered first, the EGFR-inhibitor is administered second, and the ERBB-2-inhibitor is administered third and the Src inhibitor may be administered last. Any other order of administration of the drugs is also possible. In a preferred embodiment, the Raf-MEK-ERK/EGFR/ERBB2 inhibitors are administered first and the Src inhibitor is administered last. In other words, the Raf-MEK-ERK/EGFR/ERBB2 inhibitors are administered before the Src inhibitor.

As explained above, the new use of the MEK-inhibitor, the inhibitor of at least one of EGFR and ERBB2, and at least one of the microtubule targeting agent and the Src inhibitor is not limited to combinations administered separately, but also includes the compositions obtained by physical association of the drugs and in either case a synergistic effect may be obtained. The skilled person will understand that any one of the MEK-inhibitor, the EGFR-inhibitor, the ERBB2-inhibitor and the microtubule targeting agents or the Src inhibitors, may be administrated to the patient simultaneously, separately or sequentially from the other drugs. The treatment of the patient includes treatment in the first line or second line, or third line.

In yet another example, the MEK-inhibitor, the inhibitor of at least one of EGFR and ERBB2 and the microtubule targeting drug or the Src inhibitor are administered simultaneously.

As used herein "simultaneous" administration refers to administration of more than one drug at the same time, but not necessarily via the same route of administration or in the form of one combined formulation. For example, one drug may be provided orally whereas the other drug may be provided intravenously during a patient's visit to a hospital.

In yet another example, the MEK-inhibitor, the inhibitor of at least one of EGFR and ERBB2 and the microtubule targeting drug or the Src inhibitor are administered separately. Separate administration includes the administration of the drugs in separate form and/or at separate moments in time, but again, not necessarily via the same route of administration.

In yet another example, the Raf-MEK-ERK-inhibitor, the inhibitor of at least one of EGFR and ERBB2 and the microtubule targeting drug or the Src inhibitor are administered sequentially. Sequentially indicates that the administration of a first drug is followed, immediately or in time, by the administration of the second drug.

In one embodiment, the microtubule targeting drug is one or more of vinca alkaloids, taxanes, rigosertib, volasertib (B16727), plinabulin (NPI-2358), lexibulin (Cyt9997) or related compounds, preferably is one or more of plinabulin, vinorelbine, vincristine, vinblastine, docetaxel, paclitaxel, rigosertib, the MEK-inhibitor is selumetinib, and the inhibitor of EGFR and ERBB2 is afatinib.

In one embodiment, the microtubule targeting drug is one or more of vinca alkaloids, taxanes, rigosertib, volasertib, plinabulin, lexibulin or related compounds, preferably is one or more of plinabulin, vinorelbine, vincristine, vinblastine, docetaxel, paclitaxel, rigosertib, the MEK-inhibitor is trametinib, and the inhibitor of EGFR and ERBB2 is lapatinib.

In one embodiment, the microtubule targeting drug is one or more of vinca alkaloids, taxanes, rigosertib, volasertib, plinabulin, lexibulin or related compounds, preferably is one or more of plinabulin, vinorelbine, vincristine, vinblastine, docetaxel, paclitaxel, rigosertib, the MEK-inhibitor is PD-0325901, and the inhibitor of EGFR and ERBB2 is dacomitinib.

In one embodiment, the microtubule targeting drug is docetaxel, the MEK-inhibitor is selumetinib and the inhibitor of EGFR and ERBB2 is afatinib.

In one embodiment the microtubule targeting drug is docetaxel, the MEK-inhibitor is trametinib and the inhibitor of EGFR and ERBB2 is lapatinib.

In one embodiment, the microtubule targeting drug is docetaxel, the MEK-inhibitor is PD-0325901 and the inhibitor of EGFR and ERBB2 is dacomitinib.

In one embodiment, the microtubule targeting drug is paclitaxel, the MEK-inhibitor is selumetinib and the inhibitor of EGFR and ERBB2 is afatinib.

In one embodiment, the microtubule targeting drug is paclitaxel, the MEK-inhibitor is trametinib and the inhibitor of EGFR and ERBB2 is lapatinib.

In one embodiment, the microtubule targeting drug is paclitaxel, the MEK-inhibitor is PD-0325901 and the inhibitor of EGFR and ERBB2 is dacomitinib.

In one embodiment, the microtubule targeting drug is vinorelbine, the MEK-inhibitor is selumetinib and the inhibitor of EGFR and ERBB2 is afatinib.

In one embodiment, the microtubule targeting drug is vinorelbine, the MEK-inhibitor is trametinib and the inhibitor of EGFR and ERBB2 is lapatinib.

In one embodiment, the microtubule targeting drug is vinorelbine, the MEK-inhibitor is PD-0325901 and the inhibitor of EGFR and ERBB2 is dacomitinib.

In one embodiment, the microtubule targeting drug is vincristine, the MEK-inhibitor is selumetinib and the inhibitor of EGFR and ERBB2 is afatinib.

In one embodiment, the microtubule targeting drug is vincristine, the MEK-inhibitor is trametinib and the inhibitor of EGFR and ERBB2 is lapatinib.

In one embodiment, the microtubule targeting drug is vincristine, the MEK-inhibitor is PD-0325901 and the inhibitor of EGFR and ERBB2 is dacomitinib.

In one embodiment, the microtubule targeting drug is vinblastine, the MEK-inhibitor is selumetinib and the inhibitor of EGFR and ERBB2 is afatinib.

In one embodiment, the microtubule targeting drug is vinblastine, the MEK-inhibitor is trametinib and the inhibitor of EGFR and ERBB2 is lapatinib.

In one embodiment, the microtubule targeting drug is vinblastine, the MEK-inhibitor is PD-0325901 and the inhibitor of EGFR and ERBB2 is dacomitinib.

In one embodiment, the microtubule targeting drug is plinabulin, the MEK-inhibitor is selumetinib and the inhibitor of EGFR and ERBB2 is afatinib.

In one embodiment, the microtubule targeting drug is plinabulin, the MEK-inhibitor is trametinib and the inhibitor of EGFR and ERBB2 is lapatinib.

In one embodiment the microtubule targeting drug is plinabulin, the MEK-inhibitor is PD-0325901 and the inhibitor of EGFR and ERBB2 is dacomitinib.

In one embodiment, the microtubule targeting drug is rigosertib, the MEK-inhibitor is selumetinib and the inhibitor of EGFR and ERBB2 is afatinib.

In one embodiment, the microtubule targeting drug is rigosertib, the MEK-inhibitor is trametinib and the inhibitor of EGFR and ERBB2 is lapatinib.

In one embodiment, the microtubule targeting drug is rigosertib, the MEK-inhibitor is PD-0325901 and the inhibitor of EGFR and ERBB2 is dacomitinib.

In one embodiment, the Src inhibitor is dasatinib, the MEK-inhibitor is selumetinib and the inhibitor of EGFR and ERBB2 is afatinib.

In one embodiment, the Src inhibitor is dasatinib, the MEK-inhibitor is trametinib and the inhibitor of EGFR and ERBB2 is lapatinib.

In one embodiment, the Src inhibitor is dasatinib, the MEK-inhibitor is PD-0325901 and the inhibitor of EGFR and ERBB2 is dacomitinib.

In one embodiment, the inhibitor of Src kinases is Saracatinib, the MEK-inhibitor is selumetinib and the inhibitor of EGFR and ERBB2 is afatinib.

In one embodiment, the inhibitor of Src kinases is Busitinib, the MEK-inhibitor is PD-0325901 and the inhibitor of EGFR and ERBB2 is dacomitinib.

In a second aspect, there is provided a combination comprising a MEK-inhibitor, at least one of an inhibitor of both EGFR and ERBB2 and a combination of an EGFR inhibitor and an ERBB2 inhibitor and a microtubule targeting drug or an Src inhibitor.

In one embodiment of the combination, the MEK-inhibitor is one or more of: sorafenib, PD-0325901 (Pfizer), trametinib, UO126-EtOH, PD184352, PD98059, BIX 02189, pimasertib (AS-703026, BIX 02188, TAK-733, binimetinib (MEK163, ARY-162, ARRY-2438162, PD318088, honokiol, SL-327, refametinib (RDEA119, Bay 86-9766, GDC-0623, APS-2-79-HCl, cobimetinib (GCD-0973, RG7420) (Genentech), BI-847325, AZD-8330 (AstraZeneca), RG-7167 (Roche/Chugai), RG-7304 (Roche), CIP-137401 (Cheminpharma), WX-554 (Wilex; UCB), SF-2626 (Semafore Pharmaceuticals Inc), RO-5068760 (F Hoffmann- La Roche AG), R0-4920506 (Roche), G-573 (Genentech) and G-894 (Genentech), N-acyl sulfonamide prodrug GSK-2091976A (GlaxoSmithKline), 81-847325 (Boehringer Ingelheim), WYE-130600 (Wyeth/Pfizer), ERK1-624, ERK1-2067, ERK1-23211, AD-GL0001 (ActinoDrug Pharmaceuticals GmbH), selumetinib (AZD6244), MEK-162, derivatives and salts thereof. Preferably the MEK-inhibitor is one or more of selumetinib, trametinib, or PD-0325901.

In one embodiment of the combination, the Raf1/B-raf-inhibitor is one or more of sorafinib, sorafinib tolysate, vemurafinib, dabrafinib, PLX 4720, CDC-0879, lifirafenib, Raf265, AZ628, SB590885, ZM336372, GW5074, TAK-632, CEP-32496, encorafinib, CCT196969, PLX7904, LY03009120, R05126766, MLN2480, derivatives and salts thereof.

In one In one embodiment of the combination, the ERK-inhibitor is one or more of SCH772984, ERK-IN-1, SC1, XMD8-92, LY3214996, ulixertinib (BVD-523), VRT752271, FR180204, DEL-22379, CD-0994, VX-11e, derivatives and salts thereof.

In one embodiment of the combination, the EGFR-inhibitor is one or more of: erlotinib (OSI-744), panitumumab (Abgenix), vandetanib (AstraZeneca), icotinib (hydrochloride; Beta Pharma), C0-1686 (Avila Therapeutics), AZD-4769, poziotinib (Hanmi Pharmaceutical Co Ltd), CUDC-101 (Curis), exelixis, S-222611 (Shioogi), imgatuzumab (Glycart Biotechnology AG), sapitinib, TAS-2913 (Taiho Pharmaceutical Co Ltd), theliatinib (Hutchison Medipharma Enterprises Ltd), XGFR-2421 (Glycart), HM-617138 (Hanmi Pharmaceutical Co Ltd), epitinib (Hutchison Medipharma Enterprises Ltd), NRC-2694 (Natco), MLBS-42 (ProQinase GmbH), JRP-890 (Prous Institute for Biomedical Research Sa), cetuximab, AL-6802 (Advenchen Laboratories LLC), TAK-285 (Takeda), BGB-102 (Johnson & Johnson), AEE-788 (Novartis), gefitinib, DMS-3008 (Domantis Ltd), TX-2036 (University of Tokushima), KI-6783, KI-6896 (Kirin Brewery Co Ltd), gefitinib (ZD1839), lapatinib, lapatinib ditosylate (GW-572016), afatinib (BIBW2992), neratinib, canertinib (CI-1033), AG-490, CP724714, dacomitinib (PF299804, PF299), WZ-4002, sapatinib (AZD8931), CUDC-101, AG-1478, PD153035 HCI, pelitinib (EKB-569), AC480 (BMS-599626), AEE788, AP26113-analog (ALK-IN-1), OSI-420, WZ3146, Her2 inhibitor-1, AST-1306, rociletinib (CO-1686, AVL-301), genistein, varlitinib, icotinib. WHI-P154, Daphnetin, PD168393, CNX-2006, tyrphostin 9, AG-18, osimertinib (AZD9291), olmutinib (HM61713, BI1482694), norcantharidin, EAI045, afatinib dimaleate, CL-387785 (EKI-785), lidocaine hydrochloride, nazartinib (EGF816, NVS-816), NSC228155, AZ5104, lifirafinib (BGB-283), naquotinib (ASP8273), AZD3759, and derivatives and/or salts thereof. Preferably the EGFR-inhibitor is one or more of afatinib, lapatinib or dacometinib.

In one embodiment of the combination, the ERBB2-inhibitor is one or more of: pertuzumab, trastuzumab, antibodies as described in W0-2012162561, neratinib, allitinib tosylate, CUDC-101, BT-2111, margetuximab, Exelixis, NT-004 or NT-113, S-222611, AG879, Mubritinib, AC-480, sapitinib, MM-111, PR-610, cipatinib trastuzumabduocarmycin, Prolanta, varlitinib, kahalalide F, TrasGEX, masoprocol, erbicinumab, HuMax-Her2, CP-724714, COVA-208, and pazopanib, AEE788, canertinib, pelitinib, BMS-690514, Lapatinib, Lapatinib ditosylate (GW-572016), Afatinib (BIBW2992), Neratinib, Canertinib (CI-1033), AG-490, CP724714, Sapitinib (AZD 8931), Dacomitinib (PF299804, PF299), WZ-4002, Sapatinib (AZD8931), CUDC-101, Mubritinib (TAK 165), AC480 (BMS-599626), AEE788, HER2 inhibitor 1, TAK-285, Tyrphostin AG 879, Irbinitinib (ARRAY-380, ONT-380) Poziotinib (HM781-36B), derivatives and salts thereof. Preferably the ERBB2-inhibitor is one or more of lapatinib, afatinib, or dacometinib.

In one embodiment of the combination, the EGFR-inhibitor and the ERBB2-inhibitor of the combination are the same compound and one or more of Lapatinib, Lapatinib ditosylate (GW-572016), Afatinib (BIBW2992), Neratinib, Canertinib (CI-1033), Sapitinib (AZD 8931), Dacomitinib (PF299804, PF299), CUDC-101, Mubritinib (TAK 165), TAK-285, Poziotinib (HM781-36B). Preferably the EGFR/ERBB2-inhibitor is one or more of lapatinib, afatinib, or dacometinib.

In one embodiment of the combination, the microtubule targeting drug is one or more of vinca alkaloids, taxanes, rigosertib, volasertib, plinabulin, lexibulin or derivatives thereof. Preferably the microtubule targeting drug in the combination is one or more of plinabulin, vinorelbine, vincristine, docetaxel, paclitaxel, rigosertib or vinblastine.

In one embodiment of the combination, the Src inhibitor is one or more of dasatinib, saracatinib, bosutinib, KX2-391 (KX01), NVP-BHG712, PP2, PP121, PP1, MNS (3,4-Methylenedioxy-β-nitrostyrene, MDBN), TPX-0005, WH-4-023, dasatinib monohydrate, CCT196969, MRL-1023, and derivatives and/or salts thereof. Preferably, the inhibitor of Src kinases is one or more of dasatinib, saracatinib, bosutinib, and KX2-391.

In a further embodiment, the combination of the invention is for use in the treatment of a RAS-mutant cancer. The RAS-mutant cancer, is a cancer that comprises one or more mutations in the genes: KRAS, NRAS, and HRAS, or a cancer that is resistant to drugs that are only effective in cancers that lack a RAS mutation. In other words, for cancers where a normal RAS gene is a prerequisite for a treatment option, e.g. cetuximab in colon cancer or elotinib in lung cancer, resistance to that treatment is considered to be phenotypically similar to mutant RAS cancer, and thus in our definition a mutant RAS cancer. Preferably, the RAS mutant cancer comprises a mutation in the KRAS gene. More preferably, is KRAS-mutant colon cancer, KRAS-mutant lung cancer, or KRAS-mutant pancreatic cancer.

The skilled person will understand that any one of an inhibitor of the Raf-MEK-ERK pathway, the inhibitor of at least one of EGFR and ERBB2, the microtubule targeting agents and the Src inhibitor may be administrated to the patient simultaneously, separately or sequentially from the other drugs. The treatment of the patient includes treatment in the first line or second line, or third line. As witnessed in the Examples below, the combination of such an inhibitor of the Raf-MEK-ERK pathway, at least one of an inhibitor of both EGFR and ERBB2 and a combination of an EGFR inhibitor and an ERBB2 inhibitor and a microtubule targeting drug or a Src kinase surprisingly synergistically induce apoptosis of KRAS-mutant colon cancer cells. Thus, the invention relates to a combination therapy, wherein during the therapy the patient is treated with inhibitors of MEK, at least one of EGFR and ERBB2 and a microtubule targeting agent or a Src kinase.

The combination of drugs disclosed herein will preferably be administered to the patient in a form that is suitable for administration to the patient and in a dose that is efficacious. For example, the inhibitors of the Raf-MEK-ERK pathway on the inhibitors of EGFR and/or ERBB2 are administered daily or twice daily, while the microtubule targeting agent is administered weekly or three weekly. In another example, the inhibitors of the Raf-MEK-ERK pathway on the inhibitors of EGFR and/or ERBB2 are administered daily or twice daily, while the Src inhibitor is administered weekly In a third aspect, there is provided a pharmaceutical composition comprising an inhibitor of the Raf-MEK-ERK pathway, at least one of an EGFR inhibitor and an ERBB2-inhibitor and one or more of microtubule targeting drug or one or more of Src. Preferably the inhibitor of the Raf-MEK-ERK pathway the at least one of an EGFR inhibitor and an ERBB2-inhibitor and the microtubule targeting agent or the Src Kinase, are as defined herein above. It is further preferred that the pharmaceutical composition comprises at least an inhibitor of the Raf-MEK-ERK pathway and the at least one of an EGFR inhibitor and an ERBB2-inhibitor. In a further embodiment, the pharmaceutical composition of the invention is for use in the treatment of a RAS-mutant cancer. The RAS-mutant cancer, is a cancer that comprises a mutation in the genes: KRAS, NRAS, and HRAS. Preferably, the RAS mutant cancer comprises a mutation in the KRAS gene. More preferably, the KRAS mutant cancer is KRAS-mutant colon cancer, KRAS-mutant lung cancer, or KRAS-mutant pancreatic cancer.

In a fourth aspect, the invention relates to a method for treating a RAS-mutant cancer in a subject comprising administrating to the subject an effective amount of a combination comprising an inhibitor of the Raf-MEK-ERK pathway and at least one of an inhibitor of both EGFR and ERBB2 and a combination of an EGFR inhibitor and an ERBB2 inhibitor wherein the combination is administered simultaneously, separately or sequentially with a microtubule targeting agent or a Src inhibitor.

In one embodiment, the method treatment comprises administering to a subject in need thereof the pharmaceutical composition or the combination according to the invention.

In one embodiment, the method of treatment is for treating a RAS-mutant cancer that has a mutation in the in the genes: KRAS, NRAS, and HRAS. Preferably, in the KRAS gene. Even more preferred the KRAS-mutant cancer is KRAS-mutant colon cancer, KRAS-mutant lung cancer, or KRAS-mutant pancreatic cancer.

In one embodiment, there is provided for a method for the treatment of RAS mutant cancer, wherein the method comprises simultaneous, separate or sequential administering, in a patient in need thereof, of an inhibitor of the Raf-MEK-ERK pathway, an EGFR-inhibitor, an ERBB2-inhibitor, and a microtubule targeting agent, including vinorelbine, vincristine, vinblastine, docetaxel, paclitaxel, plinabulin, rigosertib and (functionally) related products. As detailed above, also the combination may comprise the same combination of microtubule targeting drug, an inhibitor of the Raf-MEK-ERK pathway, EGFR-inhibitor and/or ERBB2-inhibitor as disclosed in the paragraphs above.

In one embodiment, there is provided for a method for the treatment of RAS mutant cancer, wherein the method comprises simultaneous, separate or sequential administering, in a patient in need thereof, of an inhibitor of the Raf-MEK-ERK pathway, an EGFR-inhibitor, and an ERBB2-inhibitor, and a Src inhibitor including dasatinib, Saracatinib, Busitinib and (functionally) related products, e.g. as described above.

The treatment of the patient includes treatment in the first line or second line, or third line.

The combination of drugs disclosed herein will preferably be administered to the patient in a form that is suitable for administration to the patient and in a dose that is efficacious, for example, in the treatment with either a microtubule targeting agent, either vinorelbine, vincristine, vinblastine, docetaxel and paclitaxel, plinabulin, rigosertib or a functionally related product, and the inhibitors of MEK, EGFR and ERBB2. Or for example in the treatment with either Src inhibitor either dasatinib, Saracatinib, Busitinib and (functionally) related products and the inhibitors of MEK, EGFR and ERBB2.

In a fifth aspect there is provided for the use of an inhibitor of the Raf-MEK-ERK pathway, an EGFR inhibitor and/or an ERBB2-inhibitor and a microtubule targeting agent, including vinorelbine, vincristine, vinblastine, docetaxel, paclitaxel, plinabulin, rigosertib and (functionally) related products, or a Src inhibitor in the manufacture of a medicament for the treatment of KRAS-mutant lung cancer or KRAS-mutant colon cancer, wherein the treatment comprises the simultaneous, separate or sequential administration of an inhibitor of the Raf-MEK-ERK pathway, EGFR-inhibitor and ERBB2-inhibitor. As detailed above, also the combination may comprise the same combination of MEK-inhibitor, EGFR-inhibitor and/or ERBB2-inhibitor as disclosed in the paragraphs above.

In a sixth aspect there is provided for an ex vivo method for testing a combination of:
a) an inhibitor of the Ras-MEK-ERK pathway;
b) at least one of an inhibitor of both EGFR and ERBB2 and a combination of an EGFR inhibitor and an ERBB2 inhibitor; and,
c) a microtubule targeting agent or a Src inhibitor,
to be used in the treatment of a patient suffering from a RAS-mutant cancer,
wherein the method comprises the step of the combined, separate or sequential addition of the combination to a tumor organoid derived from the patient and determining the effect of the combination on the growth of the tumor organoid.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the elements is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

The present invention is further described by the following examples which should not be construed as limiting the scope of the invention.

Numbered paragraphs

The following numbered paragraphs are part of the description.

1. A microtubule targeting agent, for use in the treatment of RAS-mutant cancer, wherein the microtubule targeting agent is administered simultaneously, separately or sequentially with:
a) an inhibitor of the Raf-MEK-ERK pathway; and,
b) at least one of:
  i) an inhibitor of both EGFR and ERBB2; and,
  ii) a combination of an EGFR inhibitor and an ERBB2 inhibitor.

2. A microtubule targeting agent for a use according to paragraph 1, wherein the microtubule targeting agent is one or more of a vinca alkaloid, a taxane, rigosertib, Volasertib (B16727), Plinabulin (NPI-2358), Lexibulin (Cyt9997) or derivatives thereof, and wherein preferably the microtubule targeting drug is one or more of plinabulin, vinorelbine, vincristine, docetaxel, paclitaxel, rigosertib or vinblastine.

3. A microtubule targeting agent for a use according to paragraph 1 or 2, wherein the inhibitor of the Raf-MEK-ERK pathway is one or more of:

the MEK inhibitor sorafenib, PD-0325901, Trametinib, UO126-EtOH, PD184352, PD98059, BIX 02189, Pimasertib (AS-703026, BIX 02188, TAK-733, Binimetinib (MEK163, ARY-162, ARRY-2438162, PD318088, Honokiol, SL-327, Refametinib (RDEA119, Bay 86-9766, GDC-0623, APS-2-79-HCI, Cobimetinib (GCD-0973, RG7420), BI-847325, AZD-8330 (AstraZeneca), RG-7167, RG-7304, CIP-137401, WX-554 (Wilex; UCB), SF-2626, R0-5068760, R0-4920506, G-573 and G-894, N-acyl sulfonamide prodrug GSK-2091976A, 81-84732Z, WYE-130600, ERK1-624, ERK1-2067, ERK1-23211, AD-GL0001, selumetinib, MEK-162;

the Raf/B-raf inhibitor, Sorafinib, Sorafinib tolysate, Vemurafinib, Dabrafinib, PLX 4720, CDC-0879, Lifirafenib, Raf265, AZ628, SB590885, ZM336372, GW5074, TAK-632, CEP-32496, Encorafinib, CCT196969, PLX7904, LY03009120, R05126766, MLN2480; and the ERK inhibitor SCH772984, ERK-IN-1, SC1, XMD8-92, LY3214996, Ulixertinib (BVD-523, VRT752271, FR180204, DEL-22379, CD-0994, VX-11e, and derivatives and salts thereof, and wherein preferably the inhibitor of the Raf-MEK-ERK pathway is a MEK inhibitor and wherein preferably the MEK-inhibitor is one or more of selumetinib, trametinib or PD-0325901.

4. A microtubule targeting agent for a use according to any one of the paragraphs 1-3, wherein the EGFR-inhibitor is one or more of erlotinib (OSI-744), panitumumab (Abgenix), vandetanib (AstraZeneca), icotinib (hydrochloride; Beta Pharma), C0-1686 (Avila Therapeutics), AZD-4769, poziotinib (Hanmi Pharmaceutical Co Ltd), CUDC-101 (Curis), Exelixis, S-222611 (Shioogi), imgatuzumab (Glycart Biotechnology AG), sapitinib, TAS-2913 (Taiho Pharmaceutical Co Ltd), theliatinib (Hutchison Medipharma Enterprises Ltd), XGFR-2421 (Glycart), HM-617138 (Hanmi Pharmaceutical Co Ltd), epitinib (Hutchison Medipharma Enterprises Ltd), NRC-2694 (Natco), MLBS-42 (ProQinase GmbH), JRP-890 (Prous Institute for Biomedical Research Sa), cetuximab, AL-6802 (Advenchen Laboratories LLC), TAK-285 (Takeda), BGB-102 (Johnson & Johnson), AEE-788 (Novartis), gefitinib, DMS-3008 (Domantis Ltd), TX-2036 (University of Tokushima), KI-6783, KI-6896 (Kirin Brewery Co Ltd), Gefitinib (ZD1839), lapatinib, lapatinib ditosylate (GW-572016), afatinib (BIBW2992), neratinib, canertinib (CI-1033), AG-490, CP724714, dacomitinib (PF299804, PF299), WZ-4002, sapatinib (AZD8931), CUDC-101, AG-1478, PD153035 HCI, pelitinib (EKB-569), AC480 (BMS-599626), AEE788, AP26113-analog (ALK-IN-1), OSI-420, WZ3146, Her2 inhibitor-1, AST-1306, rociletinib (CO-1686, AVL-301), genistein, varlitinib, icotinib, WHI-P154, daphnetin, PD168393, CNX-2006, tyrphostin 9, AG-18, osimertinib (AZD9291), olmutinib (HM61713, BI1482694), norcantharidin, EAI045, afatinib dimaleate, CL-387785 (EKI-785), lidocaine hydrochloride, nazartinib (EGF816, NVS-816), NSC228155, AZ5104, lifirafinib (BGB-283), naquotinib (ASP8273), AZD3759, and derivatives and/or salts thereof, and wherein preferably the EGFR-inhibitor is one or more of afatinib, lapatinib or dacometinib.

5. A microtubule targeting agent for a use according to any one of paragraphs 1-4, wherein the ERBB2-inhibitor is one or more of: pertuzumab, trastuzumab, neratinib, allitinib tosylate, CUDC-101, BT-2111, margetuximab, Exelixis, NT-004 or NT-113, S-222611, AG879, Mubritinib, AC-480, sapitinib, MM-111, PR-610, cipatinib, duocarmycin, prolanta, varlitinib, kahalalide F, TrasGEX, masoprocol, erbicinumab, HuMax-Her2, CP-724714, COVA-208, and pazopanib, AEE-788, canertinib, pelitinib, BMS-690514, Lapatinib, Lapatinib ditosylate (GW-572016), Afatinib (BIBW2992), Neratinib, Canertinib (CI-1033), AG-490, CP724714, Sapitinib (AZD 8931), Dacomitinib (PF299804, PF299), WZ-4002, Sapatinib (AZD8931), CUDC-101, Mubritinib (TAK 165), AC480 (BMS-599626), AEE788, HER2 inhibitor 1, TAK-285, Tyrphostin AG 879, Irbinitinib (ARRAY-380, ONT-380) Poziotinib (HM781-36B), derivatives and salts thereof, and wherein preferably the ERBB2-inhibitor is one or more of afatinib, lapatinib or dacometinib.

6. A microtubule targeting agent for a use according to any one of paragraphs 1-5, wherein the inhibitor of at least one of EGFR and ERBB2 is a single inhibitor that inhibits both EGFR and ERBB2 and is one of Lapatinib, Lapatinib ditosylate (GW-572016), Afatinib (BIBW2992), Neratinib, Canertinib (CI-1033), Sapitinib (AZD 8931), Dacomitinib (PF299804, PF299), CUDC-101, Mubritinib (TAK 165), TAK-285, Poziotinib (HM781-36B) derivatives and salts thereof, and wherein preferably the ERBB2-inhibitor is one or more of afatinib, lapatinib or dacometinib.

7. The microtubule targeting agent for a use according to any one of paragraphs 1-6, wherein the RAS-mutant cancer is a cancer that comprises a mutation in at least one of the KRAS, NRAS, and HRAS genes, preferably in the KRAS gene, even more preferably the RAS-mutant cancer is colon cancer, lung cancer or pancreatic cancer comprising a mutation in the KRAS gene.

8. A combination comprising a microtubule targeting drug, an inhibitor of the Raf-MEK-ERK pathway and at least one of an inhibitor of both EGFR and ERBB2 and a combination of an EGFR inhibitor and an ERBB2 inhibitor.

9. A combination according to paragraph 8, wherein the microtubule targeting agent is a microtubule targeting agent as defined in paragraph 2, wherein the inhibitor of the Raf-MEK-ERK pathway is an inhibitor of the Raf-MEK-ERK pathway as defined in paragraph 3, wherein the inhibitor of at least one of EGFR and ERBB2 is an EGFR-inhibitor is as defined in paragraph 4, an ERBB2-inhibitor as defined in paragraph 5 or inhibitor that inhibits both EGFR and ERBB2 as defined in paragraph 6.

10. A combination according to any one of paragraphs 8-9, for use in the treatment of a RAS mutant cancer.

11. A combination according to paragraph 10, wherein the RAS-mutant cancer is a cancer that comprises a mutation in at least one of the KRAS, NRAS, and HRAS genes, preferably in the KRAS gene, even more preferably the RAS-mutant cancer is colon cancer, lung cancer or pancreatic cancer comprising a mutation in the KRAS gene.

12. A method for treating a RAS-mutant cancer in a subject comprising administrating to the subject an effective amount of a microtubule targeting agent, wherein the microtubule targeting agent is administered simultaneously, separately or sequentially with:
a) at least one of an inhibitor of both EGFR and ERBB2 and a combination of an EGFR inhibitor and an ERBB2 inhibitor; and,
b) an inhibitor of the Ras-MEK-ERK pathway.

13. A method for treating a RAS mutant cancer in a subject comprising administrating to the subject an effective amount of the combination of paragraphs 8-11.

14. A method of treatment according to paragraph 12 or 13, wherein the RAS-mutant cancer is a cancer that comprises a mutation in at least one of the KRAS, NRAS, and HRAS genes, preferably in the KRAS gene, even more preferably the RAS-mutant cancer is colon cancer, lung cancer or pancreatic cancer comprising a mutation in the KRAS gene.

15. An ex vivo method for testing a combination of:
a) a microtubule targeting agent;
b) an inhibitor of the Ras-MEK-ERK pathway; and,
c) at least one of an inhibitor of both EGFR and ERBB2 and a combination of an EGFR inhibitor and an ERBB2 inhibitor;
to be used in the treatment of a patient suffering from a RAS-mutant cancer,
wherein the method comprises the step of the combined, separate or sequential addition of the combination to a tumor organoid derived from the patient and determining the effect of the combination on the growth of the tumor organoid.

16. A Src inhibitor, for use in the treatment of RAS-mutant cancer, wherein the Src inhibitor is administered simultaneously, separately or sequentially with:
a) an inhibitor of the Raf-MEK-ERK pathway; and,
b) at least one of:
  i) an inhibitor of both EGFR and ERBB2; and,
  ii) a combination of an EGFR inhibitor and an ERBB2 inhibitor.

17. A Src inhibitor for a use according to paragraph 16, wherein the Src inhibitor is one or more of dasatinib, saracatinib, bosutinib, KX2-391 (KX01), NVP-BHG712, PP2, PP121, PP1, 3,4-methyl-enedioxy-β-nitrostyrene, TPX-0005, WH-4-023, dasatinib monohydrate, CCT196969, MRL-1023, and derivatives and/or salts thereof, and wherein preferably the inhibitor of Src kinases is one or more of dasatinib, saracatinib, bosutinib, and KX2-391.

18. A Src inhibitor for a use according to paragraph 16 or 17, wherein the inhibitor of the Raf-MEK-ERK pathway is one or more of:
the MEK inhibitor sorafenib, PD-0325901, Trametinib, UO126-EtOH, PD184352, PD98059, BIX 02189, Pimasertib (AS-703026, BIX 02188, TAK-733, Binimetinib (MEK163, ARY-162, ARRY-2438162, PD318088, Honokiol, SL-327, Refametinib (RDEA119, Bay 86-9766, GDC-0623, APS-2-79-HCl, Cobimetinib (GCD-0973, RG7420), BI-847325, AZD-8330 (AstraZeneca), RG-7167, RG-7304, CIP-137401, WX-554 (Wilex; UCB), SF-2626, RO-5068760, RO-4920506, G-573 and G-894, N-acyl sulfonamide prodrug GSK-2091976A, 81-84732Z, WYE-130600, ERK1-624, ERK1-2067, ERK1-23211, AD-GL0001, selumetinib, MEK-162;
the Raf/B-raf inhibitor, Sorafinib, Sorafinib tolysate, Vemurafinib, Dabrafinib, PLX 4720, CDC-0879, Lifirafenib, Raf265, AZ628, SB590885, ZM336372, GW5074, TAK-632, CEP-32496, Encorafinib, CCT196969, PLX7904, LY03009120, R05126766, MLN2480; and
the ERK inhibitor SCH772984, ERK-IN-1, SC1, XMD8-92, LY3214996, Ulixertinib (BVD-523, VRT752271, FR180204, DEL-22379, CD-0994, VX-11e, and derivatives and salts thereof,
and wherein preferably the inhibitor of the Raf-MEK-ERK pathway is a MEK inhibitor and wherein preferably the MEK-inhibitor is one or more of selumetinib, trametinib or PD-0325901.

19. A Src inhibitor for a use according to any one of the paragraphs 16-18, wherein the EGFR-inhibitor is one or more of erlotinib (OSI-744), panitumumab (Abgenix), vandetanib (AstraZeneca), icotinib (hydrochloride; Beta Pharma), C0-1686 (Avila Therapeutics), AZD-4769, poziotinib (Hanmi Pharmaceutical Co Ltd), CUDC-101 (Curis), Exelixis, S-222611 (Shioogi), imgatuzumab (Glycart Biotechnology AG), sapitinib, TAS-2913 (Taiho Pharmaceutical Co Ltd), theliatinib (Hutchison Medipharma Enterprises Ltd), XGFR-2421 (Glycart), HM-617138 (Hanmi Pharmaceutical Co Ltd), epitinib (Hutchison Medipharma Enterprises Ltd), NRC-2694 (Natco), MLBS-42 (ProQinase GmbH), JRP-890 (Prous Institute for Biomedical Research Sa), cetuximab, AL-6802 (Advenchen Laboratories LLC), TAK-285 (Takeda), BGB-102 (Johnson & Johnson), AEE-788 (Novartis), gefitinib, DMS-3008 (Domantis Ltd), TX-2036 (University of Tokushima), KI-6783, KI-6896 (Kirin Brewery Co Ltd), Gefitinib (ZD1839), lapatinib, lapatinib ditosylate (GW-572016), afatinib (BIBW2992), neratinib, canertinib (CI-1033), AG-490, CP724714, dacomitinib (PF299804, PF299), WZ-4002, sapatinib (AZD8931), CUDC-101, AG-1478, PD153035 HCl, pelitinib (EKB-569), AC480 (BMS-599626), AEE788, AP26113-analog (ALK-IN-1), OSI-420, WZ3146, Her2 inhibitor-1, AST-1306, rociletinib (CO-1686, AVL-301), genistein, varlitinib, icotinib, WHI-P154, daphnetin, PD168393, CNX-2006, tyrphostin 9, AG-18, osimertinib (AZD9291), olmutinib (HM61713, BI1482694), norcantharidin, EAI045, afatinib dimaleate, CL-387785 (EKI-785), lidocaine hydrochloride, nazartinib (EGF816, NVS-816), NSC228155, AZ5104, lifirafinib (BGB-283), naquotinib (ASP8273), AZD3759, and derivatives and/or salts thereof, and wherein preferably the EGFR-inhibitor is one or more of afatinib, lapatinib or dacometinib.

20. A Src inhibitor fora use according to any one of paragraphs 16-19, wherein the ERBB2-inhibitor is one or more of: pertuzumab, trastuzumab, antibodies as described in W0-2012162561, neratinib, allitinib tosylate, CUDC-101, BT-2111, margetuximab, Exelixis, NT-004 or NT-113, S-222611, AG879, Mubritinib, AC-480, sapitinib, MM-111, PR-610, cipatinib trastuzumabduocarmycin, prolanta, varlitinib, kahalalide F, TrasGEX, masoprocol, erbicinumab, HuMax-Her2, CP-724714, COVA-208, and pazopanib, AEE-788, canertinib, pelitinib, BMS-690514, Lapatinib, Lapatinib ditosylate (GW-572016), Afatinib (BIBW2992), Neratinib, Canertinib (CI-1033), AG-490, CP724714, Sapitinib (AZD 8931), Dacomitinib (PF299804, PF299), WZ-4002, Sapatinib (AZD8931), CUDC-101, Mubritinib (TAK 165), AC480 (BMS-599626), AEE788, HER2 inhibitor 1, TAK-285, Tyrphostin AG 879, Irbinitinib (ARRAY-380, ONT-380) Poziotinib (HM781-36B), derivatives and salts thereof, and wherein preferably the ERBB2-inhibitor is one or more of afatinib, lapatinib or dacometinib.

21. A Src inhibitor for a use according to any one of paragraphs 16-20, wherein the inhibitor of at least one of EGFR and ERBB2 is a single inhibitor that inhibits both EGFR and ERBB2 and is one of Lapatinib, Lapatinib ditosylate (GW-572016), Afatinib (BIBW2992), Neratinib, Canertinib (CI-1033), Sapitinib (AZD 8931), Dacomitinib (PF299804, PF299), CUDC-101, Mubritinib (TAK 165), TAK-285, Poziotinib (HM781-36B) derivatives and salts thereof, and wherein preferably the ERBB2-inhibitor is one or more of afatinib, lapatinib or dacometinib.

22. The Src inhibitor for a use according to any one of paragraphs 16-20, the RAS-mutant cancer, is a cancer that comprises a mutation in at least one of the KRAS, NRAS, and HRAS genes, preferably in the KRAS gene, even more preferably the RAS-mutant cancer is colon cancer, lung cancer or pancreatic cancer comprising a mutation in the KRAS gene.

23. A combination comprising a Src inhibitor, an inhibitor of the Raf-MEK-ERK pathway and at least one of an inhibitor of both EGFR and ERBB2 and a combination of an EGFR inhibitor and an ERBB2 inhibitor.

24. A combination according to paragraph 23, wherein the Src inhibitor is a Src inhibitor as defined in paragraph 17, wherein the inhibitor of the Raf-MEK-ERK pathway is an inhibitor of the Raf-MEK-ERK pathway as defined in paragraph 18, wherein the inhibitor of at least one of EGFR and ERBB2 is an EGFR-inhibitor is as defined in paragraph 19, an ERBB2-inhibitor as defined in paragraph 20 or inhibitor that inhibits both EGFR and ERBB2 as defined in paragraph 21.

25. A combination according to any one of paragraphs 23-24, for use in the treatment of a RAS mutant cancer.

26. A combination according to paragraph 25, wherein the RAS-mutant cancer is a cancer that comprises a mutation in at least one of the KRAS, NRAS, and HRAS genes, preferably in the KRAS gene, even more preferably the RAS-mutant cancer is colon cancer, lung cancer or pancreatic cancer comprising a mutation in the KRAS gene.

27. A method for treating a RAS-mutant cancer in a subject comprising administrating to the subject an effective amount of a Src inhibitor, wherein the Src inhibitor is administered simultaneously, separately or sequentially with:
a) at least one of an inhibitor of both EGFR and ERBB2 and a combination of an EGFR inhibitor and an ERBB2 inhibitor; and,
b) an inhibitor of the Ras-MEK-ERK pathway 28. A method for treating a RAS mutant cancer in a subject comprising administrating to the subject an effective amount of the combination of paragraphs 23-26.

29. A method of treatment according to paragraph 27 or 28, wherein the RAS-mutant cancer is a cancer that comprises a mutation in at least one of the KRAS, NRAS, and HRAS genes, preferably in the KRAS gene, even more preferably the RAS-mutant cancer is colon cancer, lung cancer or pancreatic cancer comprising a mutation in the KRAS gene.

30. An ex vivo method for testing a combination of:
a) a Src inhibitor;
b) an inhibitor of the Ras-MEK-ERK pathway; and,
c) at least one of an inhibitor of both EGFR and ERBB2 and a combination of an EGFR inhibitor and an ERBB2 inhibitor;
to be used in the treatment of a patient suffering from a RAS-mutant cancer,
wherein the method comprises the step of the combined, separate or sequential addition of the combination to a tumor organoid derived from the patient and determining the effect of the combination on the growth of the tumor organoid.

DESCRIPTION OF THE FIGURES

FIG. 2: Effect of vinorelbine and docetaxel (A) and rigosertib dasatinib and paclitaxel (B) and dasatinib (C) on various combinations of MEK and EGFR/ERBB2 inhibitors at concentrations reached in the plasma when patients are treated with the recommended phase 2 doses (Van Brummelen, 2017, supra). Indicated at the top are the range of plasma concentrations reached in different patients. afa, afatinib; sel, selumetinib; lapa, lapatinib; tram, trametinib, daco, dacomitinib; PD, PD-325901.

FIG. 3: Sequential addition of drug combinations reveals that MEK/EGFR/ERBB2 inhibition prior to vinorelbine is more effective than vinorelbine treatment prior to MEK/EGFR/ERBB2 inhibition. Left; experimental set-up. Right; Colorectal cancer tumor organoids treated with sequentially added afatinib, selumetinib and vinorelbine. Similar results were obtained when either the microtubule targeting agent docetaxel or the Src Kinase dasatinib were used.

EXAMPLES

Introduction

Figure 1:
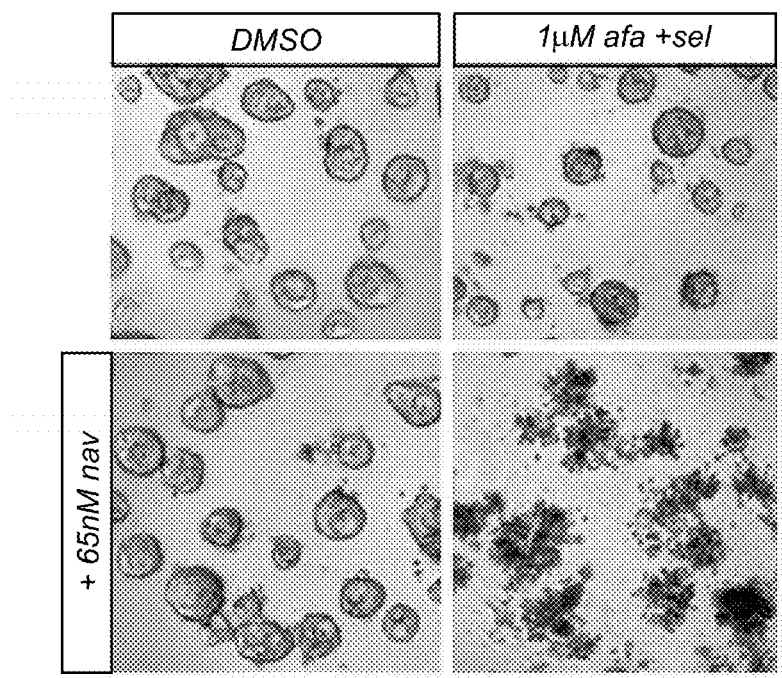
FIG. 1: Synthetic lethality screen was performed with an anti-cancer compound library. The image shows colorectal cancer tumor organoids treated with selumetinib and afatinib in the presence and absence of a low dose of navitoclax (nav), a Bcl-XL inhibitor, and the amount of apoptosis was measured by semi-automated imaging. Picture was taken after 3 days of treatment.

Currently, therapies that target the EGFR/ERBB2 are ineffective in tumors that have mutant RAS. For example, colorectal cancer patients with a tumor that have mutant KRAS are excluded from treatment with the EGFR inhibitor cetuximab (Karapetis et al., 2008). This prompted the development of therapies that target proteins that are activated by mutant Ras, particularly Raf1 and B-raf, MEK1 and 2, and ERK1 and 2. However all these drugs thus far do not show single compound efficacy in patients with RAS mutant tumors. More recently, combination therapies were developed, most notably the combination of inhibiting MEK1 and 2, with EGFR and ERBB2. The rationale behind this combination is a feedback loop that upregulates ERBB3 upon MEK inhibition of RAS mutant tumor cell lines. The kinase-impaired ERBB3 is known to form active heterodimers with other members of the ERBB family, most notably the ligand binding-impaired ERBB2. Inhibition of ERBB2 together with EGFR would inhibit this feedback pathway. Indeed, while either a MEK inhibitor or an EGFR/ERBB2 inhibitor is hardly effective on KRAS mutant colon cancer cell lines and KRAS mutant lung cancer cell lines, they strongly synergize in the inhibition of proliferation and induction of apoptosis (Sun et al., 2014, supra).

Using tumor organoids-derived from colorectal cancer patients we discovered the combination MEK inhibitor+EGFR/ERBB2 inhibitor in mutant KRAS results in a growth arrest, but hardly induces cell killing. This in contrast to KRAS normal tumor organoids that were highly sensitive to this combination. Thus, KRAS mutant colon cancer organoids remain largely resistant to this combination, predicting limited clinical effects of this combination for RAS mutant tumors (Verissimo et al., 2016, supra)

We therefore explored whether further addition of drugs may induce apoptosis in KRAS mutant colon organoids. As a proof-of-concept, we tested an apoptosis inducer, the BclXL-inhibitor navitoclax in combination with the MEK inhibitor selumetinib and the EGFR/ERBB2 inhibitor afatinib. We observe a strong synergistic effect in the induction of apoptosis. Although, this combination appears toxic for mice (Verissimo et al., 2016, supra), this result encouraged us to further search for drugs that are "synthetic lethal" to the combination MEK inhibitor+EGFR/ERBB2 inhibitor in KRAS mutant colon tumor organoids.

Material and Methods

Synthetic lethality drug screen.

Tumor organoids from colorectal cancer containing a Kras12D oncogenic mutation were treated for three days, with different concentrations of one of a 420 anti-cancer compound library (SellectChem), in the presence and absence of a combination of 1 µM selumetinib and 1 µM afatinib to inhibit MEK, EGFR and ERBB2. The induction of apoptosis was measured by semi-automated imaging. Compounds that induce apoptosis at a 5-fold lower concentration in the presence of selumetinib and afatinib, were selected for further validation.

Tumor Organoids

The tumor organoids for colon cancer used are described in (Verissimo et al., 2016, supra)

Example 1

Using KRAS mutant-containing colorectal cancer organoids, we have performed a screen with compounds that are synthetically lethal with a combination of the MEK inhibitor selumetinib and the EGFR/ERBB2 inhibitor afatinib. Organoids were treated with 1 μM selumetinib and 1 μM afatinib, together with 5 nM-20 μM of one of the 420 compounds from the anti-cancer compound library of SellectChem in 384-well plates. After three days the amount of apoptosis was measured by semi-automated imaging. As a positive control we used navitoclax, a Bcl-XL inhibitor of which we have shown previously that is functions highly synergistic with afatinib and selumetinib in the induction of mutant KRAS-containing colon cancer organoids (see FIG. 1).

When we use as a cut-off point a ΔIC50 of 100, i.e. that apoptosis is induced in the presence of selumetinib and afatinib at a concentration at least 100 fold lower than in the absence of the two drugs, we surprisingly found a number microtubule targeting drugs, most notably the vinca alkaloids vincristine and vinorelbine, the taxanes docetaxel and paclitaxel, and two unrelated compound, rigosertib and plinabulin (see Table 1). Although rigosertib has been identified as a PLK inhibitor, its anti-cancer mechanism is be the inhibition of microtubule dynamics as well (Jost et al., 2017).

TABLE 1

Results from the synthetic lethality screen using 1 μM of the EGFR/ERBB2 inhibitor afatinib plus 1 μM of the MEK inhibitor selumetinib, and a concentration range of a third drug form a the anti-cancer drug library from SelleckChem. The ΔIC50 is the fold concentration reduction of the indicated compound to get 50% killing of the organoids. >20 indicates that the compound alone did not show 50% killing at the highest concentration tested; 20 μM.

| | Anchor: afatinib + selumetinib | | |
| --- | --- | --- | --- |
| Drug added | IC50 (μM) w/o anchor | IC50 (μM) w anchor | ΔIC50 |
| Plinabulin | >20 | 0.089 | >225 |
| Vinorelbine | 5 | 0.024 | 208 |
| Vincristine | >20 | 0.008 | >2500 |
| Docetaxel | >20 | 0.046 | >435 |
| Paclitaxel | >20 | 0.047 | >425 |
| Rigosertib | >20 | 0.0135 | >1480 |

Example 2

To further validate our finding we have tested the six drugs in additional mutant KRAS containing organoids. Interestingly, although a similar synergistic effect was observed, the different organoids reacted differently. For instance, vinorelbine and vincristine were very synergistic in p19T, whereas docetaxel and paclitaxel were very synergistic in p6T (see Table 2). This implies that the optimal combination may differ between patients and indicates that organoids may be a companion diagnostic to select for the optimal combination.

TABLE 2

Validation of the various drugs in four different patient-derived colorectal cancer organoids having a mutant KRAS (see Verissimo et al., for description of the organoids)

| | Anchor: afatinib + selumetinib | | | |
| --- | --- | --- | --- | --- |
| Drug added | ΔIC50 p9T | ΔIC50 p16T | ΔIC50 p6T | ΔIC50 p18T Kras |
| Plinabulin | 8810 | 32 | 134 | 7 |
| Vinorelbine | 209 | 347 | 174 | 31 |
| Vincristine | >2500 | nd | nd | 5 |
| Docetaxel | nd | 4534 | 41531 | >435 |
| Paclitaxel | >425 | 134 | 20030 | >425 |
| Rigosertib | >1480 | 113 | 499 | 4 |

Example 3

When we use as a cut-off point a ΔIC50 of 100, i.e. that apoptosis is induced in the presence of selumetinib and afatinib at a concentration at least 100 fold lower than in the absence of the two drugs, we surprisingly found a number of inhibitors of Src kinases and/or FAK kinases, most notably dasatinib, KX2-391 and PF-573228. (Table 3).

TABLE 3

Results from the synthetic lethality screen and validation in additional organoids using 1 μM of the EGFR/ERBB2 inhibitor afatinib plus 1 μM of the MEK inhibitor selumetinib, and a concentration range of the Src kinase inhibitors dasatinib and KX2-391 and the FAK kinase inhibitor PF573228. The ΔIC50 is the fold concentration reduction of the indicated compound to get 50% killing of the organoids. >20 indicates that the compound alone did not show 50% killing at the highest concentration tested; 20 μM.

| | Organoid | | | |
| --- | --- | --- | --- | --- |
| | P9T | P16T | P6T | P26T |
| | ΔIC50 Drug added versus anchor Anchor (afatinib + selumetinib) | | | |
| | ΔIC50 | ΔIC50 | ΔIC50 | ΔIC50 |
| Dasatinib | 5701 | 13455 | 61 | 199 |
| KX2-391 | 1199 | 58 | 23 | 18 |

Example 4

Recently, van Brummelen (Van Brummelen, 2017, supra) reported recommended phase 2 doses for the combinations afatinib+selumetinib, lapatinib+trametinib, and dacomitinib+PD-0325901, as well as the range of plasma concentrations reached. We have therefore tested the synergistic effect of vinorelbine and docetaxel on combinations of MEK and EGFR/ERBB2 inhibitors at plasma level concentrations (see FIG. 2A). At these concentrations, the synergistic effect was still present. As Cmax plasma levels of docetaxel are between 1-2 μM and vinorelbine ~125 nM, we conclude that at RP2D of the MEK, EGFR/ERBB2 inhibitor combination, vinorelbine and docetaxel at concentrations below Cmax are sufficient to induce apoptosis in colorectal cancer organoids. In a further experiment we tested the microtubule targeting drugs paclitaxel and rigosertib with plasma level concentration at RP2D of afatinib+selumetinib, lapatinib+trametinib, and dacomitinib+PD-0325901. Again, we observe a strong synergistic effect at concentrations of paclitaxel and rigosertib well below their maximal tolerated plasma concentration (about 5 μM) (see FIG. 2B).

We have also tested the synergistic effect of dasatinib on combinations of MEK and EGFR/ERBB2 inhibitors at plasma level concentrations (FIG. 2C). At these concentrations, the synergistic effect was still present. As Cmax plasma levels of dasatinib are 120 nM, we conclude that at RP2D of the MEK, EGFR/ERBB2 inhibitor combination, dasatinib at concentrations below Cmax are sufficient to induce apoptosis in colorectal cancer organoids.

Example 5

We next investigated whether the combination MEK and EGFR/ERBB2 inhibitors can be given sequentially with vinorelbine or docetaxel. Colorectal cancer organoids were incubated with 1 µM afatinib and 1 µM selumetinib for two days, followed by the addition of 1 µM vinorelbine. This resulted in a rapid induction of apoptosis. A similar result was observed when after two days afatinib and selumetinib the compounds were washed out, followed by vinorelbine. Interestingly, no induction of apoptosis was observed after two days 1 µM vinorelbine, followed by 1 µM afatinib and 1 µM selumetinib (see FIG. 3). From these results we conclude that the inhibition of MEK/EGFR-MEK and EGFR/ERBB2 may prime the induction of apoptosis by vinorelbine. Similar results were obtained with docetaxel.

Further studies revealed that the synergistic effect of the MEK/EGFR/ERBB2 inhibitor combination with docetaxel rapidly declines if the time between the wash-out and the addition of docetaxel was increased to a couple of hours. From these results we conclude that the most optimal treatment schedule is first the MEK/EGFR/ERBB2 inhibitor combination followed by the addition of the microtubule targeting agent. We propose therefor for our initial clinical trial a schedule of continuous addition of the MEK/EGFR/ERBB2 inhibitor combination, with starting after two days, a weekly dose of the microtubule targeting agent.

Example 5

Previously we found that an ERK inhibitor in the combination with the EGFR/ERBB2 inhibitor afatinib results in a similar cell cycle arrest as when a MEK inhibitor is present in the combination (Verissimo et al., 2016, supra). This suggests that also replacing the MEK inhibitor for an ERK inhibitor in the triple combination with an EGFR/ERBB2 inhibitor and either a microtubule targeting agent and an inhibitor of Src Kinase would be equally effective. We are therefore testing this combination with an ERK inhibitor GDC-0994 and SCH772984, lapatinib and docetaxel, and indeed observe a similar synergism. In addition, we replace the MEK inhibitor for the Raf1/B-raf inhibitor Dabrafinib and again observe the synergistic effects. This implies that any inhibitor of the Raf-MEK-ERK pathway can replace the MEK inhibitor in the triple combination.

Example 6

The clear synergistic effect of the MEK/EGFR/ERBB2 inhibitors and the microtubule targeting agents observed in KRAS mutant organoids prompted us to test the synergistic effect of this combination in KRAS mutant lung cancer organoids and KRAS mutant pancreatic cancer organoids. We test the combination MEK/EGFR/ERBB2 inhibitors and a microtubule targeting agent as a proof of concept. We clearly observe a similar synergistic effect. From these results we conclude that inhibition of the Raf-MEK-ERK pathway and EGFR/ERBB2 in combination with a microtubule targeting agents is a treatment option for KRAS mutant lung cancer and KRAS mutant pancreatic cancer as well.

Example 7

Finally we have xenotransplanted a colorectal cancer organoid under the skin of immune-compromised mice. After the tumor reached sufficient size we continuously treated the mice with the MEK inhibitor trametinib and the EGFR/ERBB2 inhibitor lapatinib, both supplied by the drinking water. Once a week the MTA vinorelbine was given by oral gavage. First, we did not observe significant added toxicity by the addition of vinorelbine as measured by weight loss. Secondly, tumor outgrowth was complete abolished as measured by tumor size. These results are promising for further studies in men.

CONCLUSIONS

We have discovered previously that the combination an inhibitor of the Raf-MEK-ERK pathway including selumetinib, and an EGFR/ERBB2 inhibitor including afatinib, is highly cytotoxic for KRAS normal colorectal tumor organoids, but not for KRAS mutant colorectal tumor organoids (Verissimo et al., 2016, supra). Using a screen for synthetic lethality with afatinib and selumetinib, we surprisingly found (1) a number of compounds that interfere in microtubule dynamics and (2) inhibitors of Src kinases to be highly synergistic with the MEK/EGFR/ERBB2 inhibitor combination in inducing apoptosis. Most notably these compounds are the vinca alkaloids, vinorelbine and vincristine, the taxanes, docetaxel and paclitaxel and the unrelated compounds, plinabulin and rigosertib. Although rigosertib was initially identified as a PLK inhibitor, more resent evidence indicates that at effects microtubule dynamics as well (Jost et al., 2017, supra). Src kinase inhibitors include dasatinib, a drug that is used to inhibit Bcr/Abl in the treatment of chronic myeloid leukemia Three combinations of an inhibitor of the Raf-MEK-ERK pathway and an EGFR/ERBB2 inhibitor have been tested extensively in a phase1 clinical trial, afatinib and selumetinib, lapatinib and trametinib, and dacomitinib and PD-0325901. From each of these combinations the RP2D and dosing schedule have been determined. However, for colorectal cancer the trial is terminated due to the lack of response (Van Brummelen, 2017). We therefore suggest to add either one of the microtubule targeting agents or a Src kinase inhibitor to the combinations. Indeed, in all combinations we see effective cell killing at concentrations reached by the RP2D for the Raf-MEK-ERK pathway and EGRFR/ERBB2 combination, and below Cmax of vinorelbine, docetaxel, rigosertib and dasatinib. Importantly, as most of these drugs are given once a week (vinorelbine, paclitaxel) or even once in three weeks (docetaxel), our observation that pretreatment with the Raf-MEK-ERK pathway and EGFR/ERBB2 inhibitor may be sufficient to induce apoptosis, we envision a protocol in which patients are given the RP2D followed by pulses of (low concentrations) of either microtubule targeting agent or a Src inhibitor.

The experiments herein with inhibitors of MEK (MEK1 and 2) show proof-of-concept for inhibition of the Raf-MEK-ERK pathway. Oher inhibitors of the pathway, most notably inhibitors of Raf (Raf1, A-raf, B-raf and inhibitors of ERK (ERK 1 and 2) therefore also show a similar synergistic effect.

Thus far we have used mutant K-ras colorectal cancer organoids and our first clinical trial will be with patients having metastatic cancer with no further treatment options. However, if successful for colon cancer, other mutant KRAS cancers should be tested, most notably pancreatic cancer with 90% having a KRAS mutation and Non-Small Cell Lung Cancer, with 30% having a K-ras mutation.

A further conclusion of our results is that, although we clearly see synergism with all combinations tested, there is variation between patient organoids. Some organoids are very sensitive to the anchor with a taxane, (P6, Table 2), whereas other organoids are more sensitive to the anchor with vincristine or rigosertib (P9, Table 2). This may imply that organoids can be used in making the decision which combination is most effective for a particular patient.

REFERENCES

Blagoev, K. B., Wilkerson, J., Burotto, M., Kim, C., Espinal-Dominguez, E., Garcia-Alfonso, P., Alimchandani, M., Miettinen, M., Blanco-Codesido, M., and Fojo, T. (2017). Neutral evolution of drug resistant colorectal cancer cell populations is independent of their KRAS status. PLoS One 12, e0175484.
Bos, J. L. (1989). ras oncogenes in human cancer: a review. Cancer Res 49, 4682-4689.
Cox, A. D., Fesik, S. W., Kimmelman, A. C., Luo, J., and Der, C. J. (2014). Drugging the undruggable RAS: Mission possible? Nat Rev Drug Discov 13, 828-851.
Eberhard, D. A., Johnson, B. E., Amler, L. C., Goddard, A. D., Heldens, S. L., Herbst, R. S., Ince, W. L., Janne, P. A., Januario, T., Johnson, D. H., et al. (2005). Mutations in the epidermal growth factor receptor and in KRAS are predictive and prognostic indicators in patients with non-small-cell lung cancer treated with chemotherapy alone and in combination with erlotinib. J Clin Oncol 23, 5900-5909.
Hsu, H. C., Thiam, T. K., Lu, Y. J., Yeh, C. Y., Tsai, W. S., You, J. F., Hung, H. Y., Tsai, C. N., Hsu, A., Chen, H. C., et al. (2016). Mutations of KRAS/NRAS/BRAF predict cetuximab resistance in metastatic colorectal cancer patients. Oncotarget 7, 22257-22270.
Jost, M., Chen, Y., Gilbert, L. A., Horlbeck, M. A., Krenning, L., Menchon, G., Rai, A., Cho, M. Y., Stern, J. J., Prota, A. E., et al. (2017). Combined CRISPRi/a-Based Chemical Genetic Screens Reveal that Rigosertib Is a Microtubule-Destabilizing Agent. Mol Cell 68, 210-223 e216.
Karapetis, C. S., Khambata-Ford, S., Jonker, D. J., O'Callaghan, C. J., Tu, D., Tebbutt, N. C., Simes, R. J., Chalchal, H., Shapiro, J. D., Robitaille, S., et al. (2008). K-ras mutations and benefit from cetuximab in advanced colorectal cancer. N Engl J Med 359, 1757-1765.
Komlodi-Pasztor, E., Sackett, D., Wilkerson, J., and Fojo, T. (2011). Mitosis is not a key target of microtubule agents in patient tumors. Nat Rev Clin Oncol 8, 244-250.
Prior, I. A., Lewis, P. D., and Mattos, C. (2012). A comprehensive survey of Ras mutations in cancer. Cancer Res 72, 2457-2467.
Sun, C., Hobor, S., Bertotti, A., Zecchin, D., Huang, S., Galimi, F., Cottino, F., Prahallad, A., Grernrum, W., Tzani, A., et al. (2014). Intrinsic resistance to MEK inhibition in KRAS mutant lung and colon cancer through transcriptional induction of ERBB3. Cell Rep 7, 86-93.
Van Brummelen, E. (2017). Early clinical development of targetted anticancer agents. Thesis Utrecht University.
Verissimo, C. S., Overmeer, R. M., Ponsioen, B., Drost, J., Mertens, S., Verlaan-Klink, I., Gerwen, B. V., van der Ven, M., Wetering, M. V., Egan, D. A., et al. (2016). Targeting mutant RAS in patient-derived colorectal cancer organoids by combinatorial drug screening. Elife 5. e18489

The invention claimed is:
1. A method for treating a RAS-mutant cancer in a subject comprising administrating to the subject a combination comprising an inhibitor of the Raf-MEK-ERK pathway and at least one of:
  i) an inhibitor of both EGFR and ERBB2; and,
  ii) a combination of an EGFR inhibitor and an ERBB2 inhibitor,
  wherein the combination comprising the inhibitor of the Raf-MEK-ERK pathway and at least one of the inhibitor of both EGFR and ERBB2 and the combination of the EGFR inhibitor and the ERBB2 inhibitor, is administered simultaneously, separately or sequentially with:
    a) microtubule targeting agent; or
    b) a Src inhibitor.
2. The method of claim 1, wherein the microtubule targeting agent is one or more of a vinca alkaloid, a taxane, rigosertib, Volasertib (BI6727), Plinabulin (NPI-2358), Lexibulin (Cyt9997) or derivatives thereof.
3. The method of claim 1, wherein the Src inhibitor is one or more of dasatinib, saracatinib, bosutinib, KX2-391 (KX01), NVP-BHG712, PP2, PP121, PP1, MNS (3,4-Methylenedioxy-β-nitrostyrene, MDBN), TPX-0005, WH-4-023, dasatinib monohydrate, CCT196969, MRL-1023, and derivatives and/or salts thereof.
4. The method of claim 1, wherein the inhibitor of the Raf-MEK-ERK pathway is one or more of:
  the MEK inhibitor sorafenib, PD-0325901, Trametinib, UO126-EtOH, PD184352, PD98059, BIX 02189, Pimasertib (AS-703026, BIX 02188, TAK-733, Binimetinib (MEK163, ARY-162, ARRY-2438162, PD318088, Honokiol, SL-327, Refametinib (RDEA119, Bay 86-9766, GDC-0623, APS-2-79-HCl, Cobimetinib (GCD-0973, RG7420), BI-847325, AZD-8330, RG-7167, RG-7304, CIP-137401, WX-554, SF-2626, R0-5068760, R0-4920506, G-573 and G-894, N-acyl sulfonamide prodrug GSK-2091976A, 81-84732Z, WYE-130600, ERK1-624, ERK1-2067, ERK1-23211, AD-GL0001, selumetinib, MEK-162;
  the Raf/B-raf inhibitor, Sorafinib, Sorafinib tolysate, Vemurafinib, Dabrafinib, PLX 4720, CDC-0879, Lifirafenib, Raf265, AZ628, SB590885, ZM336372, GW5074, TAK-632, CEP-32496, Encorafinib, CCT196969, PLX7904, LY03009120, RO5126766, MLN2480; and
  the ERK inhibitor SCH772984, ERK-IN-1, SC1, XMD8-92, LY3214996, Ulixertinib (BVD-523, VRT752271, FR180204, DEL-22379, CD-0994, VX-11e, and derivatives and salts thereof.
5. The method of claim 1, wherein the EGFR-inhibitor is one or more of erlotinib (OSI-744), panitumumab, vandetanib, icotinib, C0-1686, AZD-4769, poziotinib, CUDC-101, S-222611, imgatuzumab, sapitinib, TAS-2913, theliatinib, XGFR-2421, HM-617138, epitinib, NRC-2694, MLBS-42, JRP-890, cetuximab, AL-6802, TAK-285, BGB-102, AEE-788, gefitinib, DMS-3008, TX-2036, K1-6783, K1-6896, Gefitinib, lapatinib, lapatinib ditosylate (GW-572016), afatinib (BIBW2992), neratinib, canertinib (CI-1033), AG-490, CP724714, dacomitinib (PF299804, PF299), WZ-4002, sapatinib (AZD8931), CUDC-101, AG-1478, PD153035 HCl, pelitinib (EKB-569), AC480 (BMS-599626), AEE788, AP26113-analog (ALK-IN-1), OSI-420, WZ3146, Her2 inhibitor-1, AST-1306, rociletinib (CO-1686, AVL-301), genistein, varlitinib, icotinib, WHI-P154, daphnetin, PD168393, CNX-2006, tyrphostin 9,

AG-18, osimertinib (AZD9291), olmutinib (HM61713, BI1482694), norcantharidin, EAI045, afatinib dimaleate, CL-387785 (EKI-785), lidocaine hydrochloride, nazartinib (EGF816, NVS-816), NSC228155, AZ5104, lifirafinib (BGB-283), naquotinib (ASP8273), AZD3759, and derivatives and/or salts thereof.

6. The method of claim 1, wherein the ERBB2-inhibitor is one or more of: pertuzumab, trastuzumab, neratinib, allitinib tosylate, CUDC-101, BT-2111, margetuximab, NT-004 or NT-113, S-222611, AG879, Mubritinib, AC-480, sapitinib, MM-111, PR-610, cipatinib trastuzumabduocarmycin, varlitinib, kahalalide F, masoprocol, erbicinumab, HuMax-Her2, CP-724714, COVA-208, and pazopanib, AEE-788, canertinib, pelitinib, BMS-690514, Lapatinib, Lapatinib ditosylate (GW-572016), Afatinib (BIBW2992), Neratinib, Canertinib (CI-1033), AG-490, CP724714, Sapitinib (AZD 8931), Dacomitinib (PF299804, PF299), WZ-4002, Sapatinib (AZD8931), CUDC-101, Mubritinib (TAK 165), AC480 (BMS-599626), AEE788, HER2 inhibitor 1, TAK-285, Tyrphostin AG 879, Irbinitinib (ARRAY-380, ONT-380) Poziotinib (HM781-36B), derivatives and salts thereof.

7. The method of claim 1, wherein the inhibitor of at least one of EGFR and ERBB2 is a single inhibitor that inhibits both EGFR and ERBB2 and is one of Lapatinib, Lapatinib ditosylate (GW-572016), Afatinib (BIBW2992), Neratinib, Canertinib (CI-1033), Sapitinib (AZD 8931), Dacomitinib (PF299804, PF299), CUDC-101, Mubritinib (TAK 165), TAK-285, Poziotinib (HM781-36B) derivatives and salts thereof.

8. The method of claim 1, wherein the RAS-mutant cancer, is a cancer that comprises a mutations in the genes: KRAS, NRAS, and HRAS.

9. A combination comprising:
a) an inhibitor of the Raf-MEK-ERK pathway; and
b) at least one of an inhibitor of both EGFR and ERBB2 and a combination of an EGFR inhibitor and an ERBB2 inhibitor,
wherein the combination comprising the inhibitor of the Raf-MEK-ERK pathway and at least one of the inhibitor of both EGFR and ERBB2 and the combination of the EGFR inhibitor and the ERBB2 inhibitor, further comprises a microtubule targeting drug or a Src inhibitor.

10. The combination according to claim 9,
wherein the microtubule targeting agent is one or more of a vinca alkaloid, a taxane, rigosertib, Volasertib (BI6727), Plinabulin (NPI-2358), Lexibulin (Cyt9997) or derivatives thereof,
wherein the Src inhibitor is one or more of dasatinib, saracatinib, bosutinib, KX2-391 (KX01), NVP-BHG712, PP2, PP121, PP1, MNS (3,4-Methylenedioxy-β-nitrostyrene, MDBN), TPX-0005, WH-4-023, dasatinib monohydrate, CCT196969, MRL-1023, and derivatives and/or salts thereof, wherein the inhibitor of the Raf-MEK-ERK pathway is one or more of:
the MEK inhibitor sorafenib, PD-0325901, Trametinib, UO126-EtOH, PD184352, PD98059, BIX 02189, Pimasertib (AS-703026, BIX 02188, TAK-733, Binimetinib (MEK163, ARY-162, ARRY-2438162, PD318088, Honokiol, SL-327, Refametinib (RDEA119, Bay 86-9766, GDC-0623, APS-2-79-HCl, Cobimetinib (GCD-0973, RG7420), BI-847325, AZD-8330, RG-7167, RG-7304, CIP-137401, WX-554, SF-2626, RO-5068760, RO-4920506, G-573 and G-894, N-acyl sulfonamide prodrug GSK-2091976A, 81-84732Z, WYE-130600, ERK1-624, ERK1-2067, ERK1-23211, AD-GL0001, selumetinib, MEK-162;
the Raf/B-raf inhibitor, Sorafinib, Sorafinib tolysate, Vemurafinib, Dabrafinib, PLX 4720, CDC-0879, Lifirafenib, Raf265, AZ628, SB590885, ZM336372, GW5074, TAK-632, CEP-32496, Encorafinib, CCT196969, PLX7904, LY03009120, RO5126766, MLN2480; and
the ERK inhibitor SCH772984, ERK-IN-1, SC1, XMD8-92, LY3214996, Ulixertinib (BVD-523, VRT752271, FR180204, DEL-22379, CD-0994, VX-11e, and derivatives and salts thereof,
and wherein the inhibitor of at least one of EGFR and ERBB2 is one or more of erlotinib (OSI-744), panitumumab, vandetanib, icotinib, CO-1686, AZD-4769, poziotinib, CUDC-101, S-222611, imgatuzumab, sapitinib, TAS-2913, theliatinib, XGFR-2421, HM-617138, epitinib, NRC-2694, MLBS-42, JRP-890, cetuximab, AL-6802, TAK-285, BGB-102, AEE-788, gefitinib, DMS-3008, TX-2036, K1-6783, K1-6896, Gefitinib (ZD1839), lapatinib, lapatinib ditosylate (GW-572016), afatinib (BIBW2992), neratinib, canertinib (CI-1033), AG-490, CP724714, dacomitinib (PF299804, PF299), WZ-4002, sapatinib (AZD8931), CUDC-101, AG-1478, PD153035 HCl, pelitinib (EKB-569), AC480 (BMS-599626), AEE788, AP26113-analog (ALK-IN-1), OSI-420, WZ3146, Her2 inhibitor-1, AST-1306, rociletinib (CO-1686, AVL-301), genistein, varlitinib, icotinib, WHI-P154, daphnetin, PD168393, CNX-2006, tyrphostin 9, AG-18, osimertinib (AZD9291), olmutinib (HM61713, BI1482694), norcantharidin, EAI045, afatinib dimaleate, CL-387785 (EKI-785), lidocaine hydrochloride, nazartinib (EGF816, NVS-816), NSC228155, AZ5104, lifirafinib (BGB-283), naquotinib (ASP8273), AZD3759, and derivatives and/or salts thereof,
or an ERBB2-inhibitor inhibitor is one or more of: pertuzumab, trastuzumab, neratinib, allitinib tosylate, CUDC-101, BT-2111, margetuximab, NT-004 or NT-113, S-222611, AG879, Mubritinib, AC-480, sapitinib, MM-111, PR-610, cipatinib trastuzumabduocarmycin, varlitinib, kahalalide F, masoprocol, erbicinumab, HuMax-Her2, CP-724714, COVA-208, and pazopanib, AEE-788, canertinib, pelitinib, BMS-690514, Lapatinib, Lapatinib ditosylate (GW-572016), Afatinib (BIBW2992), Neratinib, Canertinib (CI-1033), AG-490, CP724714, Sapitinib (AZD 8931), Dacomitinib (PF299804, PF299), WZ-4002, Sapatinib (AZD8931), CUDC-101, Mubritinib (TAK 165), AC480 (BMS-599626), AEE788, HER2 inhibitor 1, TAK-285, Tyrphostin AG 879, Irbinitinib (ARRAY-380, ONT-380) Poziotinib (HM781-36B), derivatives and salts thereof,
or wherein the inhibitor of at least one of EGFR and ERBB2 is a single inhibitor that inhibits both EGFR and ERBB2 and is one of Lapatinib, Lapatinib ditosylate (GW-572016), Afatinib (BIBW2992), Neratinib, Canertinib (CI-1033), Sapitinib (AZD 8931), Dacomitinib (PF299804, PF299), CUDC-101, Mubritinib (TAK 165), TAK-285, Poziotinib (HM781-36B) derivatives and salts thereof.

11. An ex vivo method for testing a combination of:
a) an inhibitor of the Ras-MEK-ERK pathway;
b) at least one of an inhibitor of both EGFR and ERBB2 and a combination of an EGFR inhibitor and an ERBB2 inhibitor; and,
c) a microtubule targeting agent or an Src inhibitor, to be used in the treatment of a patient suffering from a RAS-mutant cancer, wherein the method comprises the step of the combined, separate or sequential addition of the combination to a tumor organoid derived from the patient and determining the effect of the combination comprising the inhibitor of the Raf-MEK-ERK pathway, at least one of the inhibitor of both EGFR and ERBB2 and the combination of the EGFR inhibitor and the ERBB2 inhibitor and the microtubule targeting agent or the Src inhibitor, on the growth of the tumor organoid.

12. The method of claim 2, wherein the microtubule targeting agent is one or more of plinabulin, vinorelbine, vincristine, docetaxel, paclitaxel, rigosertib or vinblastine.

13. The method of claim 8, wherein the RAS-mutant cancer is a KRAS mutant colon cancer, a KRAS mutant lung cancer or a KRAS mutant pancreatic cancer.

\* \* \* \* \*